(12) United States Patent  
Beigelman et al.

(10) Patent No.: US 6,972,330 B2  
(45) Date of Patent: Dec. 6, 2005

(54) CHEMICAL SYNTHESIS OF METHOXY NUCLEOSIDES

(75) Inventors: Leonid Beigelman, Longmont, CO (US); Peter Haeberli, Berthoud, CO (US); Alexander Karpeisky, Lafayette, CO (US); David Sweedler, Louisville, CO (US)

(73) Assignee: Sirna Therapeutics, Inc., Boulder, CO (US)

( * ) Notice: Subject to any disclaimer, the term of this patent is extended or adjusted under 35 U.S.C. 154(b) by 304 days.

(21) Appl. No.: 10/431,739

(22) Filed: May 8, 2003

(65) Prior Publication Data

US 2003/0204078 A1 Oct. 30, 2003

Related U.S. Application Data

(63) Continuation of application No. 09/586,345, filed on Jun. 2, 2000, now abandoned, which is a continuation of application No. 09/361,484, filed on Jul. 26, 1999, now abandoned, which is a continuation-in-part of application No. 08/600,429, filed on Feb. 13, 1996, now abandoned.

(51) Int. Cl.[7] ............................................ C07H 19/167
(52) U.S. Cl. ................ 536/27.11; 536/27.6; 536/27.81; 536/28.5; 536/55.3
(58) Field of Search ............................ 536/27.11, 27.6, 536/27.81, 28.5, 55.3

(56) References Cited

PUBLICATIONS

Azuma and Isono, "Transnucleosidation: An Improved Method for Transglycosylation from Pyrimidines to Purines," *Chem. Pharm. Bull.* 25(12):3347–3353 (1977).
Beigelman et al., "Alternate Approaches to the Synthesis of 2′-O-Me Nucleosides," *Nucleosides & Nucleotides* 14(3–5):421–425 (1995).

Broom and Robins, "Primary Processes in the Photochemistry of Tetramethyl–1,3–cyclobutanedione," *I Am. Chem. Soc.* 87(5):1144–1146 (1965).

Chanteloup and Thuong, "Efficient Synthesis of 2–O–Alkyl Ribonucleosides Using Trichloroacetimidate D–Ribofuranosides as Ribosyl Donors," *Tetrahderon Letters* 35(6):877–880 (1994).

Chavis et al., "Synthesis of 2′, 3′–Differentiated Ribonucleosides via Glycosylation Reactions with 2–O–Me or 2–O–TBDMS Ribofuranose Derivatives. 1. Pyrimidine Series," *J. Org. Chem.* 47:202–206 (1982).

Cotten et al., "2–O–Methyl, 2′–O–ethyl oligoribonucleotides and phosphorothioate oligodeoxyribonucleotides as inhibitors of the in vitro U7 snRNP–dependent mRNA processing event," *Nucleic Acids Research* 19:2629–2635 (1991).

Davoll et al., "A New Synthesis of Purine Nucleosides. The Synthesis of Adenosine, Guanosine and 2,6–Diamino–9–β–D–Ribofuranosylpurine," *J. Am. Chem. Soc.* 73:1650–1655 (1951).

Duval–Valentin, "Specific inhibition of transcription by triple helix–forming oligonucleotides," *Proc. Natl. Acad. Sci. USA* 89:504–508 (1992).

Egholm et al., "PNA hybridizes to complementary oligonucleotides obeying the Watson–Crick hydrogen–bonding rules," *Nature* 365:566–568 (1993).

Haga et al., "3–O–Methyl–D–allose and a facile route to 2– and 3–O–methyl–D–riboses," *Carbohydrate Research* 21:440–446 (1972).

(Continued)

*Primary Examiner*—James O. Wilson
*Assistant Examiner*—Ganapathy Krishnan
(74) *Attorney, Agent, or Firm*—McDonnell Boehnen Hulbert & Berghoff LLP

(57) ABSTRACT

Process for chemical synthesis of methoxy nucleosides.

12 Claims, 9 Drawing Sheets

Synthesis of 2,2′-anhydro-1-(β-D-arabinofuranosyl)uracil i. diphenylcarbonate, NaHCO₃ / DMF 110°C
ii. MeOH reflux

OTHER PUBLICATIONS

Imazawa and Eckstein, "Facile Synthesis of 2'–Amino–2'–deoxyribofuranosyl Purines," *J. Org. Chem.* 44:2039–2041 (1979).

Inoue, Japanese Patent No. 61–291595, Dec. 22, 1986.

Inoue et al., "Synthesis and hybridization studies on two complementary nona(2'–O–methyl) ribonucleotides," *Nucleic Acids Research* 15:6131–6149 (1987).

Khwaja and Robins, "Purine Nucleosides. XVI. Synthesis of the Naturally Occurring 2'–O–Methylpurine Ribonucleosides and Related Derivatives," *Journal of the American Chemical Society* 88(15):3640–3643 (1966).

Leonard et al., "A Convenient Preparation of Protected 2'–O–Methylguanosine," *Nucleosides & Nucleotides* 11(6):1201–1204 (1992).

Limbach et al., "Summary: the modified nucleosides of RNA," Nucleic Acids Research 22(12):2183–2196 (1994).

Martin et al., "The Action of Diazomethane on Ribonucleosides. Preparation of Ribonucleoside 2'– and 3'–Methyl Ethers," *Biochemistry* 7:1406–1412 (1968).

Nair and Richardson, "Modification of Nucleic Acid Bases via Radical Intermediates: Synthesis of Dihalogenated Purine Nucleosides," *Synthesis* 8:670–672 (1982).

Parmentier et al., "A Convergent Synthesis of 2'–O–Methyl Uridine," *Tetrahedron* 50:5361–5368 (1994).

Philips and Horwitz, "Nucleosides. XVII. Benzylation–Debenzylation Studies on Nucleosides," *J. Org. Chem.* 40(12):1856–1858 (1975).

Robins et al., "Nucleic Acid Related Compounds. 12. The Facile and High Yield Stannous Chloride Catalyzed Monomethylation of the Cis–Glycol System of Nucleoside by Diazomethane," *J. Org. Chem.* 13:1891–1899 (1974).

Robins et al., "Nucleic acid related compounds. 36. Synthesis of the 2'–O–methyl and 3'–O–methyl ethers of guanosine and 2–aminoadenosine and correlation of O–methylnucleoside $^{13}C$ nmr spectral shifts," *Canadian Journal of Chemistry* 59:3360–3364 (1981).

Ross et al., "General Preparative Synthesis of 2'–O–Methylpyrimidine Ribonucleosides," *J. Heterocyclic Chem.* 31:765–769 (1994).

Scaringe et al., "Chemical synthesis of biologically active oligoribonucleotides using β–cyanoethyl protected ribonucleoside phosphoramidites," Nucl Acids Res. 18:5433–5441 (1990).

Sproat and Gait, "Ch. 4—Solid–phase Synthesis of Oligodeoxyribonucleotides by the Phosphotriester Method," in *Oligonucleotide Synthesis: A Practical Approach,* edited by Gait, IRL Press, Oxford, UK, pp. 83–115 (1984).

Sproat et al., "New synthetic routes to protected purine 2'–O'methylriboside–3'–O–phosphoramidites using a novel alkylation procedure," *Nucleic Acids Research* 18:41–49 (1990).

Srivastava et al., U.S. Patent No. 5,214,135, issued May 25, 1993, "N–Protected–2'–O–Methyl–Ribonucleosides and N–Protected 2'–O–Methyl–3'–Cyanoethyl–N,–N–Diisopropyl Phosphoramidite Ribonucleosides".

Stein and Cheng, "Antisense Oligonucleotides as Therapeutic Agents—Is the Bullet Really Magical?" *Science* 261:1004–1288 (1993).

Torrence et al., "Targeting RNA for degradation with a (2'–5') oligoadenylate–antisense chimera," *Proc. Natl. Acad. Sci USA* 90:1300–1304 (1993).

Ueda, "Ch. 1—Synthesis and Reaction of Pyrimidine Nucleosides," *Chemistry of Nucleosides and Nucleotides* vol. 1, pp. 1–112, Townsend editor, Plenum Press, New York, New York (1988).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Verheyden et al., "Synthesis of Some Pyrimidine 2'–Amino–2'–deoxynucleosides," *J. Org. Chem.* 36:250–254 (1971).

Wincott et al., "Synthesis, deprotection, analysis and purification of RNA and ribozymes," Nucleic Acids Research 23(14):2677–2684 (1995).

Yamauchi et al., "Methylation of Nucleosides with Trimethylsulfonium Hydroxide. Effects of Transition Metal Ions, "*J. Org. Chem.* 45:3865–3868 (1980).

Synthesis of 2,2'-anhydro-1-(β-D-arabinofuranosyl)uracil i. diphenylcarbonate, NaHCO₃ / DMF 110°C
ii. MeOH reflux

Synthesis of 2'-O-Methyl Uridine i. B(OCH₃)₃, BF₃•MeOH / MeOH
ii. B(OCH₃)₃ / MeOH

Synthesis of 2'-O-Methyl Cytidine iii. a. B(OCH$_3$)$_3$ / MeOH
    b. Ac$_2$O / DMF iv. a. B(OCH$_3$)$_3$, BF$_3$•MeOH / MeOH
    b. Ac$_2$O / DMF

3'-O-Methyl Pyrimidine Nucleosides i. B(OCH$_3$)$_3$, BF$_3$•MeOH / MeOH
ii. B(OCH$_3$)$_3$ / MeOH

R=H, CH$_3$
R$_1$=OH, H

5'-O-Methyl Pyrimidine Nucleosides i. $B(OCH_3)_3$, $BF_3 \cdot MeOH$ / MeOH
ii. $B(OCH_3)_3$ / MeOH

R=H, $OCH_3$
$R_1$=OH, H

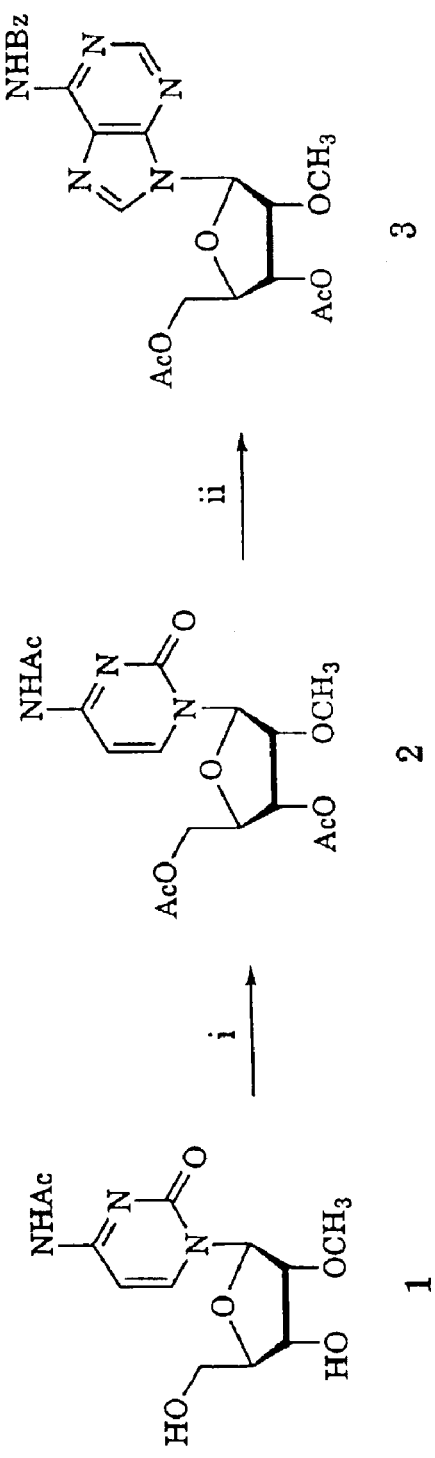

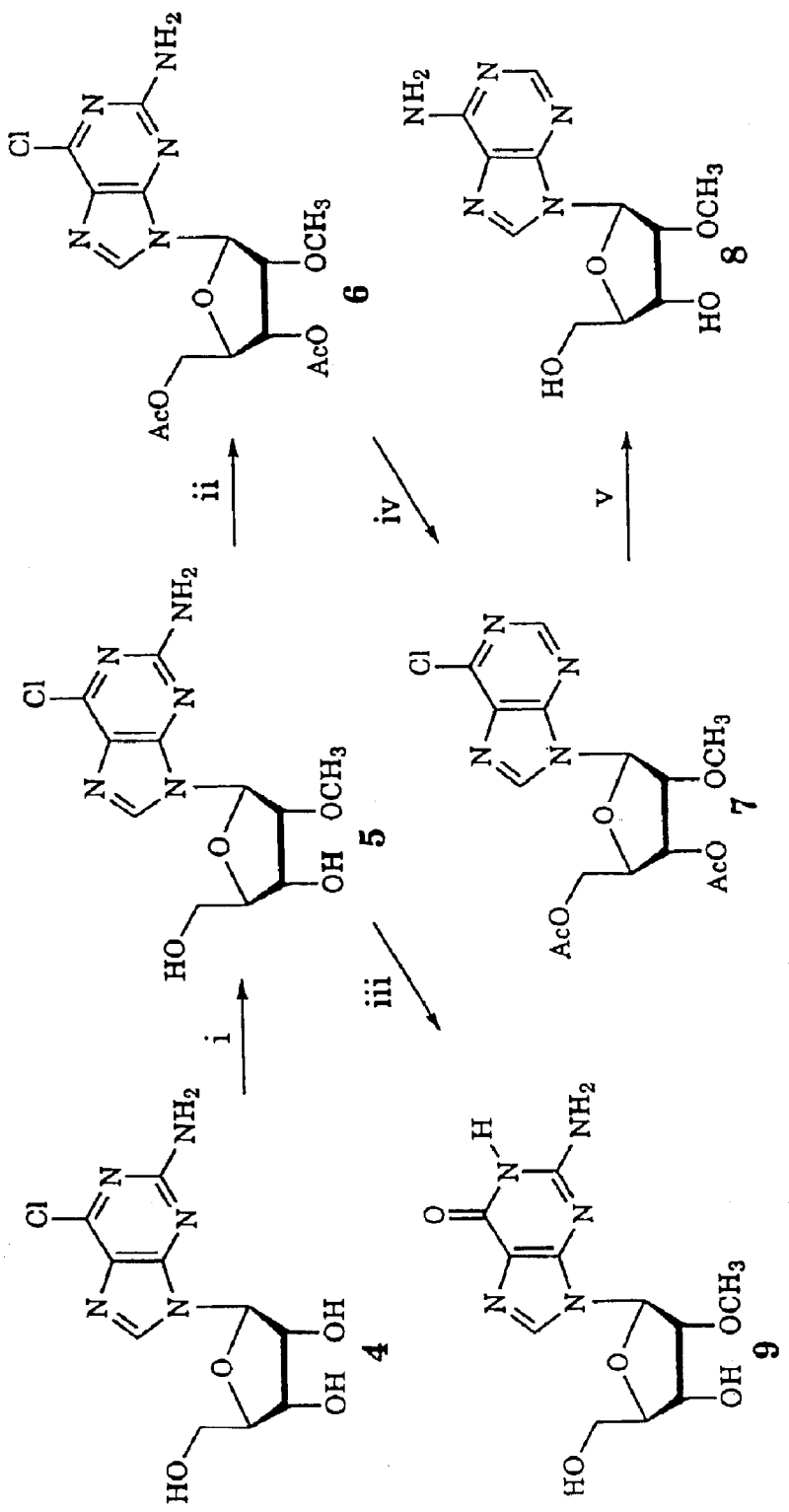
FIG. 8. Synthesis of 2'-O-Methyl- A &-G
i) NaH/ MeI/DMF; ii) Ac₂O, DMAP, Et₃N/ CH₃CN; iii) DABCO/water;
iv) isoamylnitrite/THF; v) NH₃/MeOH

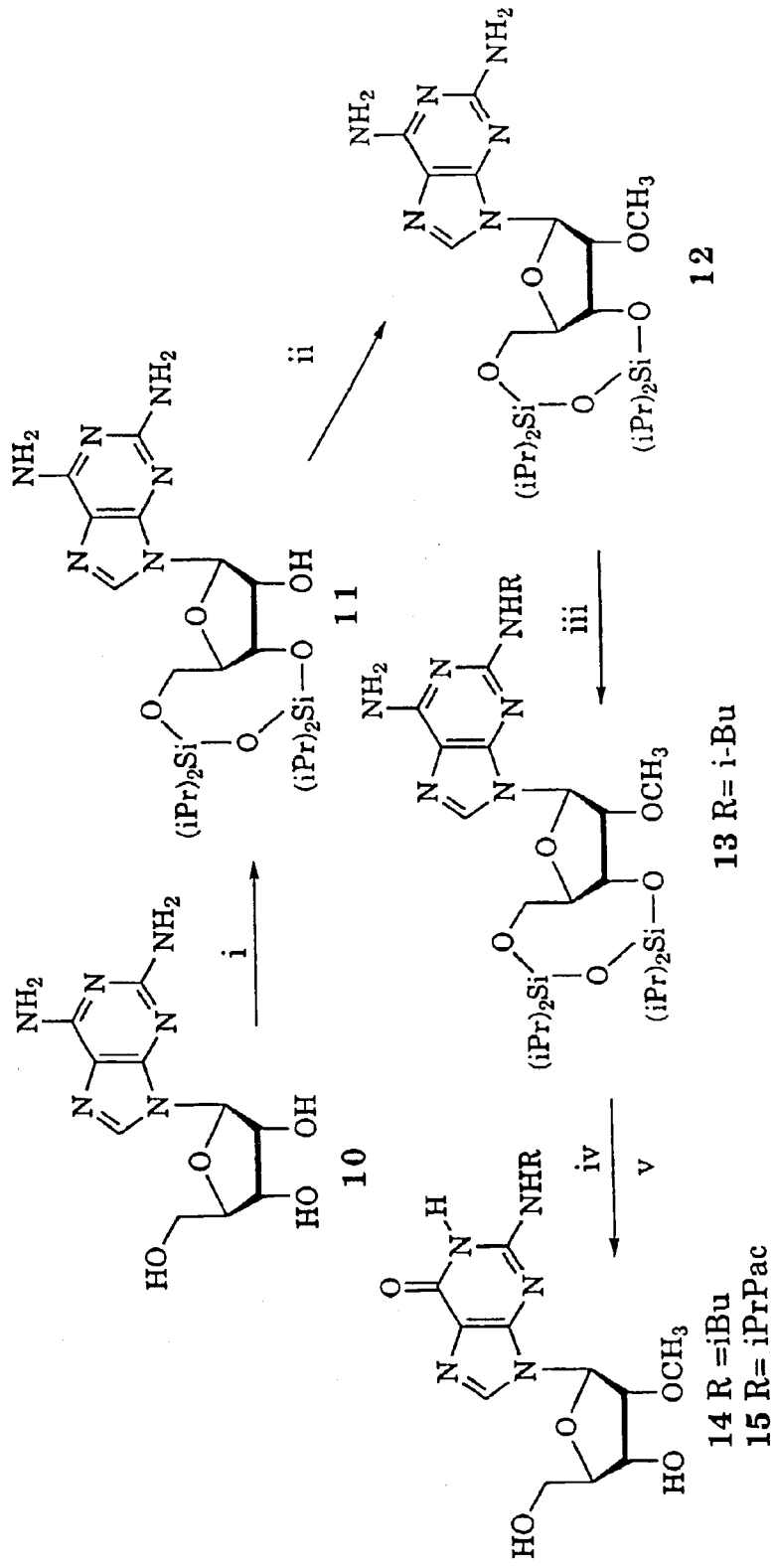
FIG. 9. Synthesis of 2'-O-methyl guanosine
i. TIPSCl/pyridine; ii. MeI, NaH/DMF 0°C; iii. iPrPACCl/pyridine or iBuCl/pyridine; iv. HOAc, NaNO₂/H₂O; v. TEA•3HF

CHEMICAL SYNTHESIS OF METHOXY NUCLEOSIDES

This patent application is a continuation of Beigelman et al., U.S. Ser. No. 09/586,345, filed Jun. 2, 2000, now abandoned, which is a continuation Beigelman et al., U.S. Ser. No. 09/361,484, filed Jul. 26, 1999, now abandoned, and this application is also a continuation-in-part of Beigelman et al., U.S. Ser. No. 08/600,429 filed Feb. 13, 1996 now abandoned. These applications are hereby incorporated by reference herein in their entirety including the drawings.

BACKGROUND OF THE INVENTION

This invention relates to the chemical synthesis of 2'-O-methyl, 3'-O-methyl and 5'-O-methyl nucleosides.

The following is a brief description of synthesis of methoxy nucleosides. This summary is not meant to be complete but is provided only for understanding of the invention that follows. This summary is not an admission that all of the work described below is prior art to the claimed invention.

Sugar modifications, such as 2'-O-methyl, have been discovered in a variety of naturally occurring RNA (e.g., tRNA, mRNA, rRNA; reviewed by Hall, 1971 The Modified Nucleosides in Nucleic Acids, Columbia University Press, New York; Limbach et al., 1994 Nucleic Acids Res. 22, 2183). In an attempt to understand the biological significance, structural and thermodynamic properties, and nuclease resistance of these sugar modifications in nucleic acids, several investigators have chemically synthesized nucleosides, nucleotides and phosphoramidites containing various sugar modifications and incorporated them into oligonucleotides. There are several reports in the literature describing the synthesis of 2'-O-methyl nucleosides, 2-O-methyl nucleotides, 2'-O-methyl phosphoramidites and oligonucleotides containing 2'-O-methyl substitutions (Broom and Robins, 1965 J. Am. Chem. Soc. 87, 1145; Martin et al., 1968 Biochemistry, 7, 1406; Robins et al., 1974 J. Org. Chem. 39, 1891; Inoue et al., 1987 Nucleic Acids Res. 15, 6131; Cotten et al., 1991 Nucleic Acids Res. 19, 2629; Andrews et al., 1994 J. Heterocyclic Chem. 31, 765; Beigelman et al., 1995 Nucleosides & Nucleotides 14, 421; Sproat et al., 1990 Nucleic Acids Res. 18, 41).

Broom and Robins, 1965 J. Am. Chem. Soc. 87, 1145 and Martin et al., 1968 Biochemistry, 7, 1406, describe the synthesis of 2'-O-methyl ribonucleotides involving monomethylation of a 2',3'-cis-diol system of a ribonucleoside with diazomethane. This procedure gives rise to a mixture of 2'- and 3'-O-methyl nucleosides in 20–40% combined yield. The two isomers are then separated by ion-exchange chromatography.

Robins et al., 1974 J. Org. Chem. 39, 1891, describe the treatment of a methanolic solution of uridine with diazomethane (in glyme) in the presence of stannous chloride dihydrate (in methanol) to synthesize 2'-O-methyluridine (58% yield). This reaction also yielded a significant fraction (28%) of 3'-O-methyluridine which is purified away from the 2'-O-methyl form by chromatography.

Inoue, Japanese Patent Publication No. 61291595 and Inoue et a., 1987 Nucleic Acids Res. 15, 613, describe a process for the synthesis of 2'-O-methyl ribonucleosides involving alkylation of 3',5'-O-(tetraisopropyldisiloxane-1, 3-diyl) (TIPDS)-ribonucleosides with methyl iodide. Inoue et al., state that (page 6133, second main paragraph):

"Treatment of 3',5'-O-TIDPS-uridine (1) with benzoyl chloride . . . in N,N-dimethylacetamide in the presence of triethylamine . . . selectively gave the $N^3$-benzoylated derivative (2) in 70.5% yield. Then, 2 was treated with $CH_3I$ . . . in benzene in the presence of $Ag_2O$ . . . at 40° C. overnight to give the $N^3$-benzoyl-2'-O-methyl derivative (3, 84.5%). Debenzoylation of 3 with dil. $NH_4OH$ followed by removal of TIPDS group with 0.5N HCl afforded 2'-O-methyluridine . . . in 84% yield."

Srivastava and Roy, U.S. Pat. No. 5,214,135, describe the synthesis of 2'-O-methyl nucleosides using an approach similar to Inoue et al., supra, except that the reaction with methyl iodide/silver oxide was carried out at 25° C. for 24–46 hr with an 80–86% yield. This reaction, similar to the one described by Inoue et al., supra, also gave rise to the 3'-O-methyl isomer in 6–8% yield.

Parmentier et al., 1994 Tetrahedron 50, 5361, describe a convergent synthesis of 2'-O-methyl uridine. This procedure uses a multi-step process involving—"a facile obtention of the 2'-O-methyl sugar synthon using totally selective and efficient methylation conditions; . . . a stereoselective highyield condensation with an uracil derivative, yielding the desired β-form with a satisfactory anomeric excess." (page 5361, fifth paragraph).

Chanteloup and Thuong, 1994 Tetrahedron Letters 35, 877, describe synthesis of 2'-O-alkyl ribonucleosides using trichloroacetimidate D-ribofuranosides as ribosyl donors. They state in the abstract on page 877—

"Trichloroacetimidate-2-O-alkyl-3,5-O-TIPS-β-D-ribofuranoside glycosylates silylated nucleobases in a fast high-yielding and stereoselective reaction promoted by trimethylsilyl trifluoromethanesulfonate. This method has been applied to the synthesis of 2'-O-alkyl ribonucleosides further transformed to building blocks ready for oligo(2'-O-alkyl) ribonucleotide construction."

Beigelman et al., 1995 Nucleosides & Nucleotides 14, 421, describe three different approaches to the synthesis of 2'-O-methyl nucleosides. They state that—

Method 1:

"Retrosynthetic analysis showed that 3-O-alkylated derivatives of 1,2:5,6-di-O-isopropylidene(IP)-α-D-allofuranose (1) could be transformed to the related 2'-alkyl ribofuranosides by selective degradation of the C1–C2 bond with subsequent cyclization of the generated C2-formyl group to the C5-OH." (Page 421, third paragraph)

Method 2:

"The 3'-O-TBDMS-derivatives of protected ribonucleosides are byproducts obtained during the preparation of 2'-O-TBDMS derivatives—key building blocks in oligoribonucleotide synthesis. At the same time, 3'-O-TBDMS-isomers could be useful starting compounds in the preparation of 2'-O-methyl-3'-O-phosphoramidites. We explored this possibility on cytidine derivative 14. Reaction of 3'-O-TBDMS-5'-O-DMT-$N^4$-i-Bu-cytidine (14) with $Ag_2O$—$CH_3I$ using a modified method of Ohtsuka et al. (supra) yielded 3'-O-TBDMS-5'-O-DMT-$N^4$-i-Bu-2'-O-methyl cytidine (15) in 26% yield. The 2'-O-TBDMS isomer 16 was also obtained (22% yield) along with the starting 3'-O-isomer (18%). When 2'-O-TBDMS-5'-O-DMT-$N^4$-i-Bu-cytidine (16) was subjected to the same reaction conditions, the same mixture of products was obtained. These results show that under the above reaction conditions migration of the TBDMS group accompanies the methylation reaction and methylation takes place selectively at the 2'-OH position." (Page 422, second full paragraph)

Method 3:

"Among different methods of indirect introduction of a methyl group, the use of 1-alkylthioalkyl intermediates seems to be the most promising. Although methods of synthesis of methylthiomethyl ethers of nucleosides and carbohydrates are well developed, their transformation into a methyl group sometimes requires additional steps. We were interested in the testing of more reactive methylthiophenyl ethers as precursors for methyl ethers. We found that methylthiophenyl ethers could be smoothly introduced by treating appropriately protected nucleosides or carbohydrates with PhSMe/ $Bz_2O_2$ in the presence of DMAP. Nucleoside 19 afforded methythiophenyl ether 20 in 65–70% yield, and α-ribofuranose 21 was transformed into β-furanose 22 in 60% yield. Different attempts to radically ($Bu_3SnH$, $Bz_2O^2$) reduce the thiophenyl group of furanose 22 were not successful, providing only starting material. However, under the same conditions, nucleoside 20 afforded 2'-O-Me derivative 24 in 70% yield.

Haga et al., 1972 *Carbohydrate Res.* 21, 440 describe a "facile route" to the synthesis of 2- and 3-O-methyl-D-ribose from 3-O-methyl-D-allose.

Nair et al., 1982, *Synthesis* 8, 670, describes modification of nucleic acid bases via radical intermediates.

Leonard et al., 1992, *Nucleosides & Nucleotides*, 11, 1201, describe a method for the preparation of protected 2'-O-methylguanosine. This procedure is distinct from the one described in the instant invention.

Wagner et al., 1991, *Nucleic Acids Res.*, 19, 5965, describes a method for alkylation of ribonucleosides.

The information disclosed in the references cited above are distinct from the presently claimed invention since they do not disclose and/or contemplate the processes for the synthesis of the methoxy nucleosides as claimed in the instant invention.

SUMMARY OF THE INVENTION

It has been postulated (Ueda, in *Chemistry of Nucleosides and Nucleotides* ed. L. B Townsend, v.1 Plenum Press 1988 pp.1–95) that protonation of the $N_3$ atom of 2,2'-, 2,3' or 2,5'-anhydro pyrimidine nucleosides facilitates anhydro ring opening by different nucleophiles producing, in most cases, nucleoside analogs containing modifications in the carbohydrate portion of the nucleoside. Complexation of the $N_3$ atom of the above-mentioned anhydro derivatives with Lewis acids [e.g. $B(OMe)_3$] would provide the same effect directly or in the case of methanolysis, complexation of the MeOH with Lewis acids would acidify the related proton leading to potential protonation of the $N_3$ atom of the above-mentioned anhydro derivatives. Applicant investigated methanolysis of 2,2'-, 2,3' or 2,5'-anhydro pyrimidine nucleosides in the presence of a Lewis acid, such as $B(OMe)_3$ and/or $BF_3.MeOH$. The reaction involving a 2,2'-anhydro-1(β-D-arabinofuranosyl) nucleoside, such as 2,2'-anhydro-1(β-D-arabinofuranosyl) uracil or 2,2'-anhydro-1 (β-D-arabinofuranosyl) cytosine, with $B(OMe)_3$ and/or $BF_3.MeOH$, results in the production of 2'-O-methyl nucleosides with a yield of about 90–100%.

By "Lewis Acid" is meant a substance that can accept an electron pair from a base. Examples of Lewis acids are, $B(OCH_3)_3$, $BF_3$, $AlCl_3$, and $SO_3$.

In one aspect, the invention features a process for the synthesis of a 2'-O-methyl adenosine nucleoside, comprising the step of contacting a solution of $N^4$-acetyl-5',3'-di-O-acetyl-2'-O-methyl cytidine with a Lewis acid under conditions suitable for the formation of said nucleoside.

In another aspect, the invention features a process for the synthesis of 2'-O-methyl guanosine nucleoside, comprising the steps of: a) methylating 2-amino-6-chloropurine riboside by contacting said 2-amino-6-chloropurine riboside with sodium hydride, dimethylformamide and methyl iodide under conditions suitable for the formation of 2'-O-methyl-2-amino-6-chloropurine riboside; b) contacting said 2'-O-methyl-2-amino-6-chloropurine riboside with 1,4-diazabicyclo(2.2.2) octane and water under conditions suitable for the formation of said 2'-O-methyl guanosine nucleoside in a crude form; and c) purifying said 2'-O-methyl guanosine nucleoside from said crude form.

In another aspect, the invention features a process for the synthesis of 2'-O-methyl adenosine nucleoside, comprising the steps of: a) methylating 2-amino-6-chloropurine.riboside by contacting said 2-amino-6-chloropurine riboside with sodium hydride, dimethylformamide and methyl iodide under conditions suitable for the formation of 2'-O-methyl-2-amino-6-chloropurine riboside; b) contacting said 2'-O-methyl-2-amino-6-chloropurine riboside with acetic anhydride, 4-dimethylaminopyridine and triethylamine under conditions suitable for the formation of 3',5'-di-O-acetyl-2'-O-methyl-6-chloro-2-aminopurine riboside; c) deaminating said 3',5'-di-O-acetyl-2'-O-methyl-6-chloro-2-aminopurine riboside with isoamyl nitrite and tetrahydrofuran to form 3',5'-di-O-acetyl-2'-O-methyl-6-chloropurine; d) aminating said 3',5'-di-O-acetyl-2'-O-methyl-6-chloropurine with ammonia to form 2'-O-methyl adenosine nucleoside in a crude form; and e) purifying said 2'-O-methyl adenosine nucleoside from said crude form.

In yet another aspect, the invention features a process for the synthesis of 2'-O-methyl guanosine nucleoside, comprising the steps of: a) contacting 2,6-diaminopurine nucleoside with anhydrous pyridine and tetraisopropyl D-silyl chloride under conditions suitable for the formation of 2,6-diamino-9-(3,5-O-tetraisopropyldisiloxane-(1,3-diyl)-β-D-ribofuranosyl) purine; b) methylating said 2,6-Diamino-9-(3,5-O-tetraisopropyldisiloxane-(1,3-diyl)-β-D-ribofuranosyl) purine by contacting said 2,6-Diamino-9-(3,5-O-tetraisopropyldisiloxane-(1,3-diyl)-β-D-ribofuranosyl) purine with anhydrous DMF and methyl iodide under conditions suitable for the formation of 2,6-Diamino-9-(3,5-O-tetraisopropyldisiloxane-(1,3-diyl)-2'-O-methyl-β-D-ribofuranosyl) purine; c) acylating said 2,6-Diamino-9-(3, 5-O-tetraisopropyldisiloxane-(1,3-diyl)-2-O-methyl-β-D-ribofuranosyl) purine by contacting said 2,6-Diamino-9-(3, 5-O-tetraisopropyldisiloxane-(1,3-diyl)-2-O-methyl-β-D-ribofuranosyl) purine with anhydrous pyridine and isobutyryl chloride under conditions suitable for the formation of 2,6-Diamino-$N^2$-isobutyryl-9-(3,5-O-tetraisopropyldisiloxane-(1,3-diyl)-2'-O-methyl-β-D-ribofuranosyl) purine; d) deaminating and desilylating said 2,6-Diamino-$N^2$-isobutyryl-9-(3,5-O-tetraisopropyldisiloxane-(1,3-diyl)-2-O-methyl-β-D-ribofuranosyl) purine under conditions suitable for the formation of $N^2$-isobutyryl-2'-O-methyl guanosine nucleoside in a crude form; e) purifying said $N^2$-isobutyryl-2'-O-methyl guanosine nucleoside from said crude form; and f) deblocking said $N^2$-isobutyryl-2'-O-methyl guanosine nucleoside under suitable conditions to form said 2'-O-methyl guanosine nucleoside.

In one aspect, the invention features a process for the synthesis of 2'-O-methyl guanosine nucleoside, comprising the steps of: a) contacting 2,6-diaminopurine nucleoside with anhydrous pyridine and tetraisopropyl D-silyl chloride (TIPSCI) under conditions suitable for the formation of 2,6-Diamino-9-(3',5'-O-tetraisopropyldisiloxane-(1,3-diyl)-

β-D-ribofuranosyl) purine; b) methylating said 2,6-Diamino-9-(3,5-O-tetraisopropyldisiloxane-(1,3-diyl)-β-D-ribofuranosyl) purine by contacting said 2,6-Diamino-9-(3,5-O-tetraisopropyldisiloxane-(1,3-diyl)-β-D-ribofuranosyl) purine with anhydrous DMF and methyl iodide under conditions suitable for the formation of 2,6-Diamino-9-(3',5'-O-tetraisopropyldisiloxane-(1,3-diyl)-2'-O-methyl-β-D-ribofuranosyl) purine; c) acylating said 2,6-Diamino-9-(3,5-O-tetraisopropyldisiloxane-(1,3-diyl)-2-O-methyl-β-D-ribofuranosyl) purine by contacting said 2,6-Diamino-9-(3,5-O-tetraisopropyldisiloxane-(1,3-diyl)-2-O-methyl-β-D-ribofuranosyl) purine with anhydrous pyridine and isopropylphenoxyacetyl chloride under conditions suitable for the formation of 2,6-Diamino-N$^2$-isopropylphenoxyacetyl-9-(3,5-O-tetraisopropyldisiloxane-(1,3-diyl)-2-O-methyl-β-D-ribofuranosyl) purine; d) deaminating and desilylating said 2,6-Diamino-N$^2$-isopropylphenoxyacetyl-9-(3,5-O-tetraisopropyldisiloxane-(1,3-diyl)-2-O-methyl-β-D-ribofuranosyl) purine under conditions suitable for the formation of N$^2$-isopropylphenoxyacetyl-2'-O-methyl guanosine nucleoside in a crude form; e) purifying said N$^2$-isopropylphenoxyacetyl-2'-O-methyl guanosine nucleoside from said crude form; and f) deblocking said N$^2$-isopropylphenoxyacetyl-2'-O-methyl guanosine nucleoside under suitable conditions to form said 2'-O-methyl guanosine nucleoside.

In one aspect, the invention features a process for the synthesis of 2'-O-methyl guanosine nucleoside, comprising the steps of: a) contacting guanosine with N,N-dimethylformamide dibenzyl acetal under conditions suitable for the formation of N1-benzyl guanosine; b) methylating said N1-benzyl guanosine by contacting said N1-benzyl guanosine with silver acetylacetonate, trimethylsulphonium hydroxide and dimethylformamide under conditions suitable for the formation of N1-benzyl-2'-O-methyl guanosine in a crude form; c) purifying said N1-benzyl-2'-O-methyl guanosine from said crude form; d) removing the N1-benzyl protection from said N1-benzyl-2'-O-methyl guanosine by contacting said N1-benzyl-2'-O-methyl guanosine with sodium naphthalene under conditions suitable for the formation of 2'-O-methyl guanosine nucleoside in a crude form; and e) purifying said 2'-O-methyl guanosine from said crude form.

In yet another aspect, the invention features a process for the synthesis of 2'-O-methyl adenosine nucleoside, comprising the steps of: a) methylating adenosine by contacting said adenosine with dimethylformamide, silver acetylacetonate and trimethylsulphonium hydroxide under conditions suitable for the formation of 2'-O-methyl adenosine in a crude form; and b) purifying said 2'-O-methyl adenosine from said crude form.

In one aspect, the invention also features a process for the synthesis of 2'-O-methyl guanosine nucleoside, comprising the steps of: a) contacting guanosine with N,N-dimethylformamide dibenzyl acetal under conditions suitable for the formation of N1-benzyl guanosine; b) methylating said N1-benzyl guanosine by contacting said N1-benzyl guanosine with magnesium acetylacetonate, trimethylsulphonium hydroxide and dimethylformamide under conditions suitable for the formation of N1-benzyl-2'-O-methyl guanosine in a crude form; c) purifying said N1-benzyl-2'-O-methyl guanosine from said crude form; d) removing the N1-benzyl protection from said N1-benzyl-2'-O-methyl guanosine by contacting said N1-benzyl-2'-O-methyl guanosine with sodium naphthalene under conditions suitable for the formation of 2'-O-methyl guanosine nucleoside in a crude form; and e) purifying said 2'-O-methyl guanosine nucleoside from said crude form.

In one aspect, the invention features a process for the synthesis of 2'-O-methyl adenosine nucleoside, comprising the steps of: a) methylating adenosine by contacting said adenosine with dimethylformamide, magnesium acetylacetonate and trimethylsulphonium hydroxide under conditions suitable for the formation of 2'-O-methyl adenosine in a crude form; and b) purifying said 2'-O-methyl adenosine from said crude form.

In one aspect, the invention features a process for the synthesis of 2'-O-methyl adenosine nucleoside, comprising the steps of: a) methylating adenosine by contacting said adenosine with dimethylformamide, strontium acetylacetonate and trimethylsulphonium hydroxide under conditions suitable for the formation of 2'-O-methyl adenosine in a crude form; and b) purifying said 2'-O-methyl adenosine from said crude form.

In one aspect, the invention features a process for the synthesis of 2'-O-methyl guanosine nucleoside, comprising the steps of: a) contacting 2,6-diaminopurine nucleoside with anhydrous pyridine and TIPSCI under conditions suitable for the formation of 2,6-diamino-9-(3',5'-O-tetraisopropyldisiloxane-(1,3-diyl)-β-D-ribofuranosyl) purine; b) methylating said 2,6-Diamino-9-(3,5-O-tetraisopropyldisiloxane-(1,3-diyl)-β-D-ribofuranosyl) purine by contacting said 2,6-Diamino-9-(3',5'-O-tetraisopropyldisiloxane-(1,3-diyl)-β-D-ribofuranosyl) purine with anhydrous DMF and methyl iodide under conditions suitable for the formation of 2,6-Diamino-9-(3,5-O-tetraisopropyldisiloxane-(1,3-diyl)-2-O-methyl-β-D-ribofuranosyl) purine; c) acylating said 2,6-Diamino-9-(3,5-O-tetraisopropyldisiloxane-(1,3-diyl)-2-O-methyl-β-D-ribofuranosyl) purine by contacting said 2,6-Diamino-9-(3,5-O-tetraisopropyldisiloxane-(1,3-diyl)-2-O-methyl-β-D-ribofuranosyl) purine with anhydrous pyridine and isobutyryl chloride under conditions suitable for the formation of 2,6-Diamino-N$^2$-isobutyryl-9-(3,5-O-tetraisopropyldisiloxane-(1,3-diyl)-2-O-methyl-β-D-ribofuranosyl) purine; d) deaminating and desilylating said 2,6-Diamino-N$^2$-isobutyryl-9-(3,5-O-tetraisopropyldisiloxane-(1,3-diyl)-2'-O-methyl-β-D-ribofuranosyl) purine under conditions suitable for the formation of N2-isobutyryl-2'-O-methyl guanosine nucleoside in a crude form; and e) purifying said N2-isobutyryl-2'-O-methyl guanosine nucleoside from said crude form.

In yet another embodiment, the invention features a process for the synthesis of 2'-O-methyl guanosine nucleoside, comprising the steps of: a) contacting 2,6-diaminopurine nucleoside with anhydrous pyridine and TIPSCI under conditions suitable for the formation of 2,6-Diamino-9-(3,5-O-tetraisopropyldisiloxane-(1,3-diyl)-β-D-ribofuranosyl) purine; b) methylating said 2,6-Diamino-9-(3,5-O-tetraisopropyldisiloxane-(1,3-diyl)-β-D-ribofuranosyl) purine by contacting said 2,6-Diamino-9-(3,5-O-tetraisopropyldisiloxane-(1,3-diyl)-β-D-ribofuranosyl) purine with anhydrous DMF and methyl iodide under conditions suitable for the formation of 2,6-Diamino-9-(3,5-O-tetraisopropyldisiloxane-(1,3-diyl)-2-O-methyl-β-D-ribofuranosyl) purine; c) acylating said 2,6-Diamino-9-(3,5-O-tetraisopropyldisiloxane-(1,3-diyl)-2-O-methyl-β-D-ribofuranosyl) purine by contacting said 2,6-Diamino-9-(3,5-O-tetraisopropyldisiloxane-(1,3-diyl)-2'-O-methyl-β-D-ribofuranosyl) purine with anhydrous pyridine and isopropylphenoxyacetyl chloride under conditions suitable for the formation of 2,6-Diamino-N$^2$-isopropylphenoxyacetyl-9-(3',5'-O- tetraisopropyldisiloxane-(1,3-diyl)-2'-O-methyl-β-D-ribofuranosyl) purine; d) deaminating and desilylating said 2,6-Diamino-N²-isopropylphenoxyacetyl-9-(3,5-O-tetraisopropyldisiloxane-(1,3-diyl)-2-O-methyl-β-D-ribofuranosyl) purine under conditions suitable for the formation of N²-isopropylphenoxyacetyl-2'-O-methyl guanosine nucleoside in a crude form; and e) purifying said N²-isopropylphenoxyacetyl-2'-O-methyl guanosine nucleoside from said crude form.

This invention features an improved and economical synthetic method for the preparation of 2'-O-methyl nucleosides in high yield. The method is not only cost efficient, but can be scaled up to several hundred gram quantities. The method generally utilizes inexpensive commercially available 2,2'-anhydro-1(β-D-arabinofuranosyl) nucleoside, such as 2,2'-anhydro-1(β-D-arabinofuranosyl)uracil or 2,2'-anhydro-1(β-D-arabinofuranosyl)cytosine, as a starting material which is converted in a one or two step reaction sequence to 2'-O-methyl nucleosides with a yield of about 90–100%.

The 2'-O-methyl or 3'-O-methyl nucleosides can be used for chemical synthesis of nucleotides, nucleotide-triphosphates and/or phosphoramidites as a building block for selective incorporation into oligonucleotides. These oligonucleotides can be used as an antisense molecule, 2–5A antisense chimera, triplex molecule or as an enzymatic nucleic acid molecule. The oligonucleotides can also be used as probes or primers for synthesis and/or sequencing of RNA or DNA.

By "antisense" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

By "2–5A antisense chimera" it is meant, an antisense oligonucleotide containing a 5' phosphorylated 2'-5'-linked adenylate residues. These chimeras bind to target RNA in a sequence-specific manner and activate a cellular 2–5A-dependent ribonuclease which, in turn, cleaves the target RNA (Torrence et al., 1993 *Proc. Natl. Acad. Sci. USA* 90, 1300).

By "triplex DNA" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "enzymatic nucleic acid" it is meant a nucleic acid molecule capable of catalyzing reactions including, but not limited to, site-specific cleavage and/or ligation of other nucleic acid molecules, cleavage of peptide and amide bonds, and trans-splicing.

In preferred embodiments, the invention features a method for chemical synthesis of 2'-O-methyl or 3'-O-methyl nucleosides in which 2,2'-anhydro-1(β-D-arabinofuranosyl) cytosine, 2,2'-anhydro-1(β-D-arabinofuranosyl) uracil, 2,3'-anhydro-1(β-D-arabinofuranosyl) uracil, or 2,3'-anhydro-1(β-D-arabinofuranosyl) cytosine is used as the starting material, and wherein said starting material is reacted with a Lewis acid.

Another preferred embodiment of the invention features a method for chemical synthesis of 5'-O-methylpyrimidine nucleoside in which 2,5'-anhydro-1(β-D-arabinofuranosyl) pyrimidine is used as the starting material and is reacted with a Lewis acid.

In yet another preferred embodiment, the invention features novel processes for the synthesis of 2'-O-methyl purine nucleosides.

Other features and advantages of the invention will be apparent from the following description of the preferred embodiments thereof, and from the claims.

DESCRIPTION OF THE PREFERRED EMBODIMENTS

The drawing will first briefly be described.

FIG. 6 shows NMR profile of 2'-O-methyl nucleosides. A) 2'-O-methyl Uridine nucleoside. B) 2'-O-methyl cytidine nucleoside.

FIG. 7 is a diagrammatic representation of a scheme for the synthesis of 2'-O-methyl adenosine nucleoside.

FIG. 8 is a diagrammatic representation of a scheme for the synthesis of 2'-O-methyl adenosine and guanosine nucleosides.

FIG. 9 is a diagrammatic representation of a scheme for the synthesis of 2'-O-methyl guanosine nucleoside.

Figure 10:
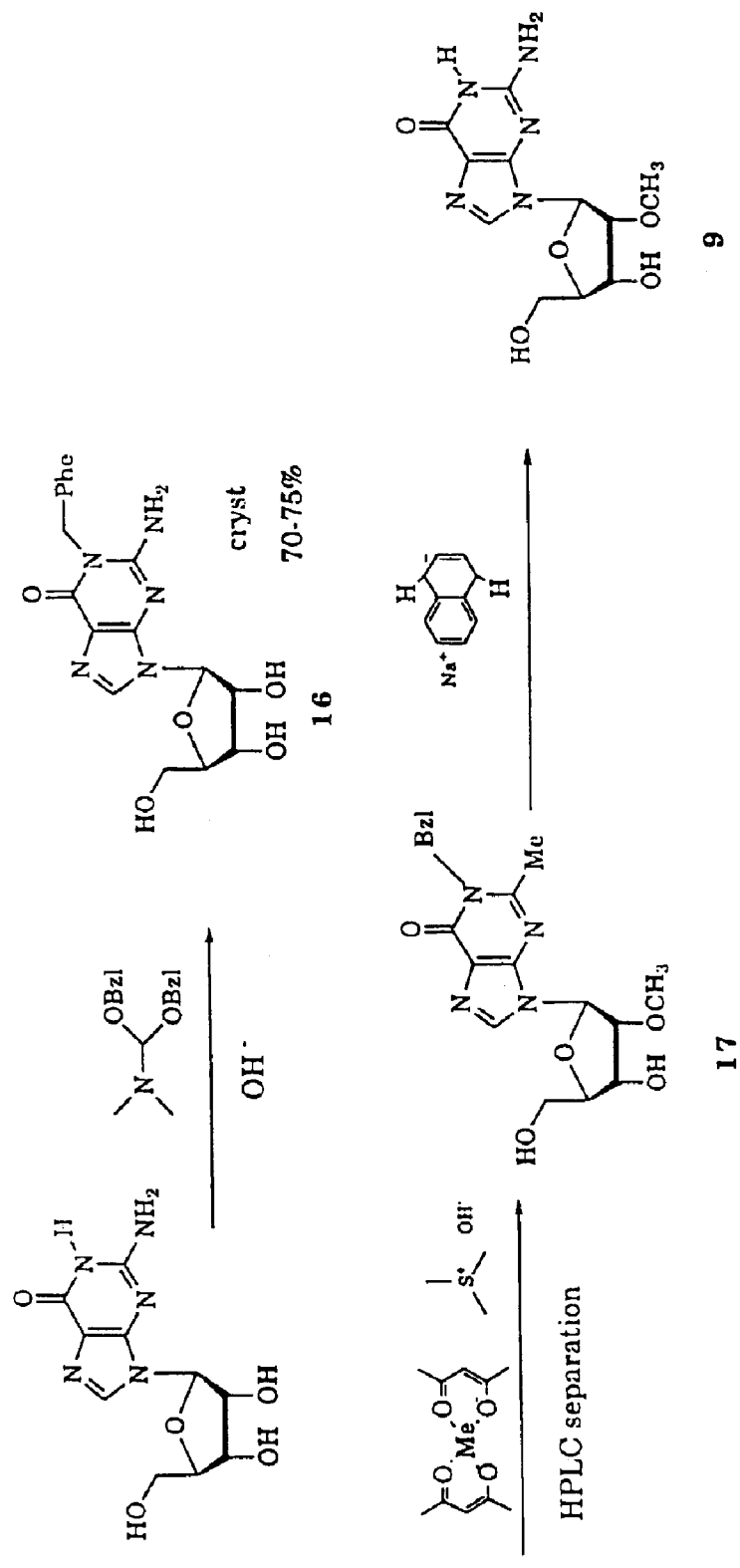

FIG. 10 is a diagrammatic representation of a scheme for the synthesis of methoxy nucleosides via N1-Benzyl guanosine route.

EXAMPLE 1

Synthesis of 2,2'-anhydro-1(β-D-arabinofuranosyl) uracil (2)

2,2'-anhydro-1(β-D-arabinofuranosyl) uracil (2) can either be purchased from Sigma Chemicals or can be synthesized using the scheme described by Verheyden et al., 1971 (*J. Org. Chem.* 36, 250). Briefly, to an oven baked 1 L 3-neck round bottom flask equipped with mechanical stirrer, reflux condenser, and positive pressure of argon, 200 g (0.819 mol) of uridine (1) was added. The reaction was carried out in the presence of diphenylcarbonate (191.2 g, 0.9 mol), and DMF (300 ml). The resulting light yellow suspension was heated to 90° C. at which time sodium bicarbonate (2.0 g) was added. The reaction mixture was then heated to 110° C. for two hours during which time $CO_2$ evolved. Over this two hour period, the reaction mixture transformed from a slurry to a homogeneous solution and back to a slurry. Upon cooling to −10° C., the reaction mixture was filtered and the filter bed washed with ethanol and cold methanol. The filter bed was then suspended in methanol (500 ml) and heated to reflux for three hours. After cooling to −10° C., the reaction mixture was filtered. The filter bed was washed with cold methanol and dried to retrieve 2 as an off white solid (140 g; 76%).

EXAMPLE 2

Synthesis of 2'-O-methyl uridine (3)

To an oven baked stainless steel bomb (300 ml), equipped with magnetic stirrer and purged with argon, 40 ml anhydrous methanol was added followed by the addition of 2,2'-anhydro-1-(β-D-arabinofuranosyl)uracil 2 (1.0 g, 4.42 mmol). To the resulting slurry, 5.0 ml trimethylborate (44.2 mmol) was added followed by the addition of boron trifluoride-methanol (50%) (1.5 ml, 8.84 mmol). The bomb was then sealed and heated in an oil bath at 130° C. for 18 hours. Upon cooling, the resulting clear, slightly colored reaction mixture was evaporated in vacuo to yield a dark foam. The crude foam was dissolved in minimal methanol/dichloromethane and applied to a flash silica gel column. A gradient of 10–30% EtOH in dichloromethane afforded 3 as a white foam (1.05 g, 92%).

Alternately, to an oven baked stainless steel bomb (920 ml), equipped with magnetic stirrer and purged with argon, 200 ml anhydrous methanol was added followed by the addition of 2 (50 g, 0.221 mol). Trimethylborate (400 ml, 3.54 mol) was added to the resulting slurry and the bomb was sealed. The bomb was then heated in an oil bath at 130° C. for 38 hours. Upon cooling, the resulting clear, slightly colored reaction mixture was evaporated in vacuo to afford an off white foam. Crystallization of the crude product from (methanol/ethyl acetate) gave pure 3 (56.8 g, 100%).

Figure 6A:
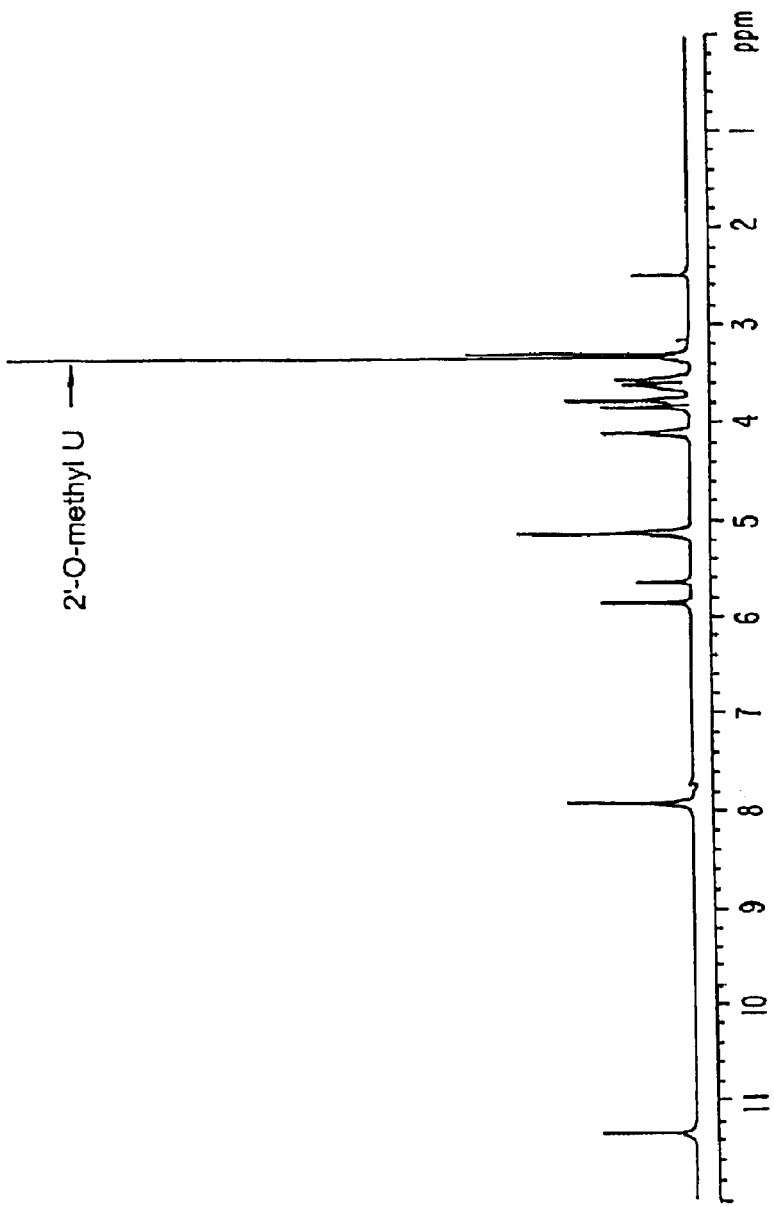

The identity and purity of the synthesized compound was confirmed by standard NMR analysis (FIG. 6A). Following is the result of NMR analysis:

$^1$H NMR DMSO: 11.33 (exch. s, 1H, NH), 7.92 (d, $J_{6,5}$=8.2, 1H, H6), 5.85 (d, $J_{1',2'}$=5.2, 1H, H1'), 5.65 (d, $J_{5,6}$=8.2, 1H, H5), 5.13 (exch. m, 2H, 5'OH, 3'OH), 4.10 (t, $J_{3',2'}$=4.9, $J_{3',4'}$=4.6, 1H, H3'), 3.85 (m, 1H, H4'), 3.62 (dd, $J_{5',4'}$=3.0, $J_{5',5''}$=12.1, 1H, H5'), 3.54 (dd, $J_{5'',4'}$=3.1, $J_{5'',5'}$=12.1, 1H, H5''), 3.35 (s, 3H, OCH$_3$). The peak corresponding to the 2'-O-methyl is indicated in the FIG. 6A.

EXAMPLE 3

2'-O-methyl cytidine (5)

To an oven baked stainless steel bomb (300 mL), equipped with magnetic stirrer and purged with argon, 50 ml anhydrous methanol was added followed by the addition of commercially available 1 g 2,2'-Anhydro-1-(β-D-arabinofuranosyl)cytosine.acetate (Aldrich) 4 (3.5 mmol). To the resulting slurry, 8 ml Trimethylborate (70 mmol) was added in the presence or absence of boron trifluoride-methanol (50%) (1.5 ml, 8.84 mmol). The bomb was sealed and then heated in an oil bath at 130° C. for 38–48 hours. Upon cooling, the resulting clear, slightly colored reaction mixture was evaporated in vacuo to afford an off white foam. After drying in vacuo, the crude foam was dissolved in anhydrous DMF (50 ml) and acetic anhydride (0.36 ml, 3.85 mmol) which was added drop-wise to the reaction mixture. The resulting clear, light yellow solution was stirred overnight at room temperature. The reaction mixture was evaporated in vacuo. Crystallization of the crude product from (methanol/ethyl acetate) gave a pure compound 5 (0.94 g, 90%).

Figure 6B:
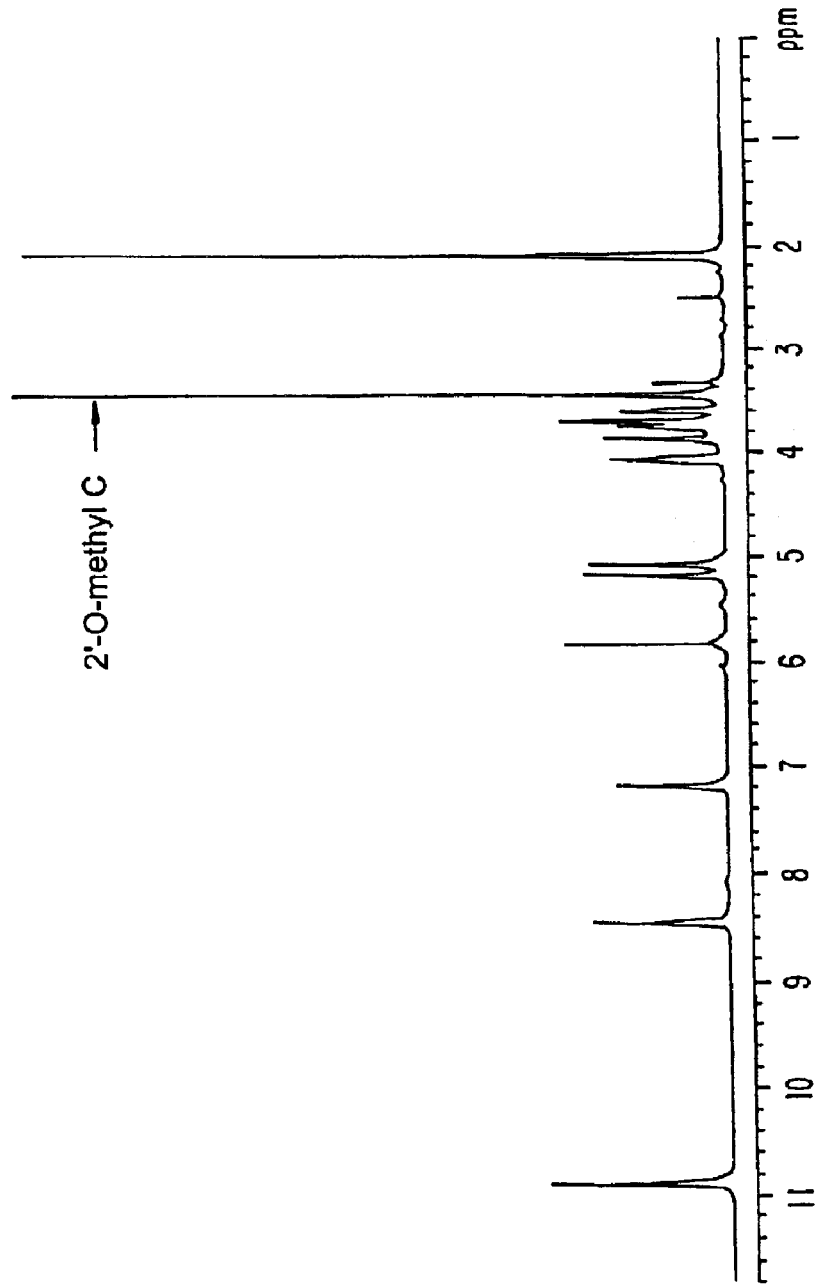

The identity and purity of the synthesized compound was confirmed by standard NMR analysis (FIG. 6B). Following is the result of NMR analysis:

$^1$H NMR DMSO: 10.89 (exch. s, 1H, NH), 8.46 (d, $J_{6,5}$=7.4, 1H, H6), 7.18 (d, $J_{5,6}$=7.4, 1H, H5), 5.83 (d, $J_{1',2'}$=2.5, 1H, H1'), 5.18 (exch. t, $J_{OH,5'}$=4.6, $J_{OH,5''}$=4.9, 1H, 5'OH), 5.08 (exch. d, $J_{OH,3'}$=6.7, 1H, 3'OH), 4.04 (t, $J_{3',2'}$=4.9, $J_{3',4'}$=6.8, 1H, H3'), 3.88 (m, 1H, H4'), 3.75 (dd, $J_{5',4'}$=2.3, $J_{5',5''}$=12.2, 1H, H5'), 3.59 (dd, $J_{5'',4'}$=2.5, $J_{5'',5'}$=12.2, 1H, H5''), 3.45 (s, 3H, OCH$_3$), 2.10 (s, 3H, CH$_3$).

2'-O-methyl nucleosides of the present invention can be readily converted into phosphoramidites using standard procedures and phosphoramidites can be readily incorporated into oligonucleotides, such as RNA, using standard procedures described in Sproat & Gait, 1984 in *Oligonucleotide Synthesis: A Practical Approach*, ed. Gait, M. J. (IRL, Oxford), pp 83–115; Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684.

EXAMPLE 4

Synthesis of 3'-O-methyl Pyrimidine Nucleoside

Figure 1:
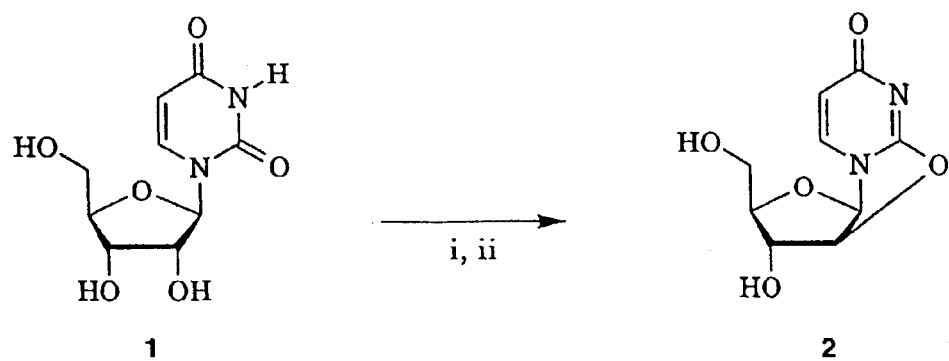
FIG. 1 is a diagrammatic representation of a scheme involved in the synthesis of 2,2'-anhydro-1(β-D-arabinofuranosyl) uracil (2).
Figure 2:
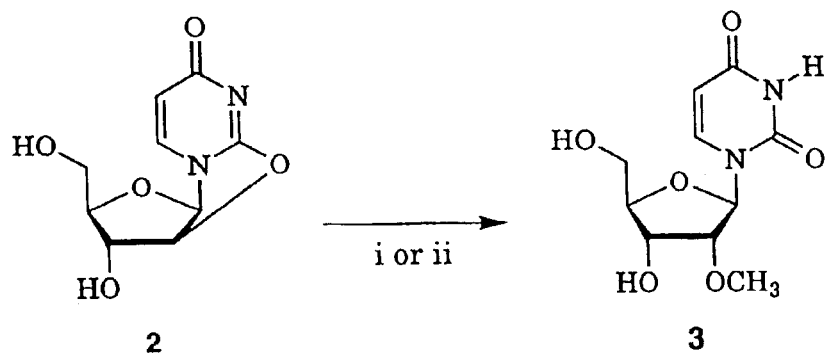
FIG. 2 is a diagrammatic representation of a scheme involved in the synthesis of 2'-O-methyl uridine (3) by the method of this invention.
Figure 3:
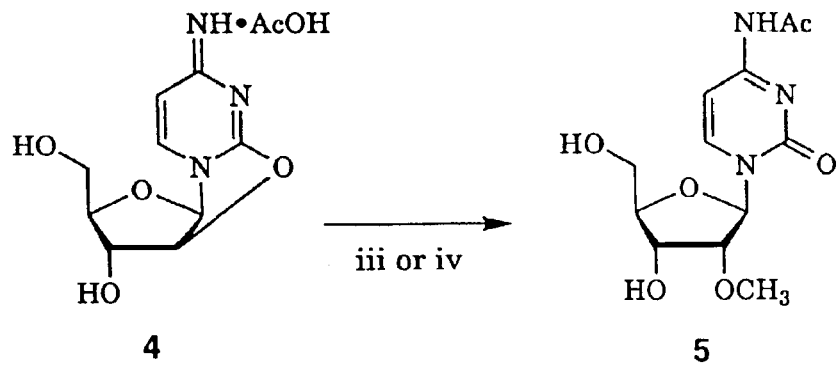
FIG. 3 is a diagrammatic representation of a scheme involved in the synthesis of 2'-O-methyl cytidine (5) by the method of this invention.
Figure 4:
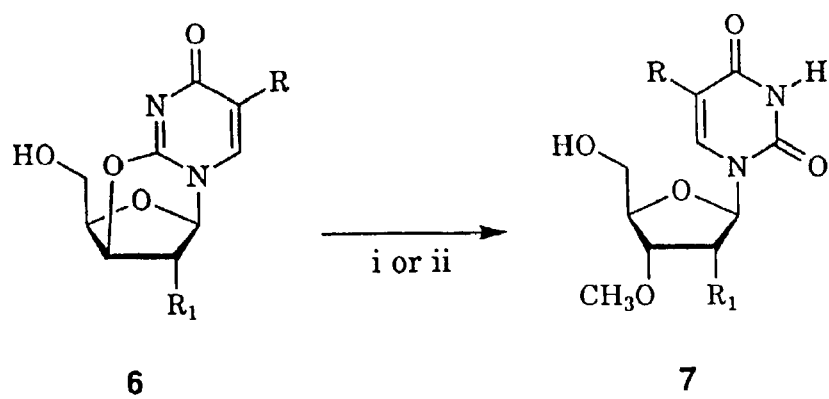
FIG. 4 is a diagrammatic representation of a scheme involved in the synthesis of 3'-O-methylpyrimidine nucleosides.

Referring to FIG. 4, the treatment of 2,3'-anhydro-1-(β-D-arabinofuranosyl)primidine 6 (Aldrich) with anhydrous methanol and trimethylborate, in the presence or absence of boron trifluoride-methanol, in an oven baked stainless steel bomb purged with argon, followed by heating in an oil bath at 130° C. for 18–48 hours, as described above, will yield 3'-O-methyl pyrimidine nucleoside 7.

EXAMPLE 5

Synthesis of 5'-O-methyl Pyrimidine Nucleoside

Figure 5:
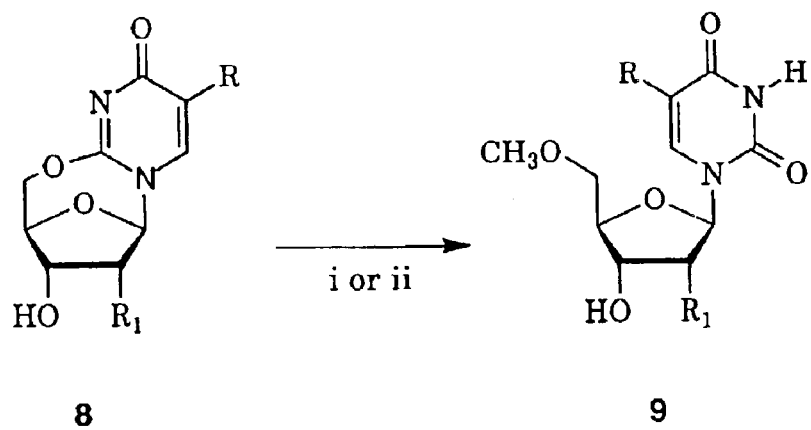
FIG. 5 is a diagrammatic representation of a scheme involved in the synthesis of 5'-O-methylpyrimidine nucleosides.

Referring to FIG. 5, the treatment of 2,5'-anhydro-1-(β-D-arabinofuranosyl)primidine 8 (Aldrich) with anhydrous methanol and trimethylborate, in the presence or absence of boron trifluoride-methanol, in an oven baked stainless steel bomb which is purged-with argon, followed by heating in an oil bath at 130° C. for 18–48 hours, as described above, will yield 5'-O-methylpyrimidine nucleoside 9.

EXAMPLE 6

Synthesis of 2'-O-Me-Adenosine via transglycosilation (Scheme 1; FIG. 7)

In 1982, Imbach et al., (*J. Org. Chem.* 1982, 47, 202) demonstrated utilization of 2'-O-methyl-1,3,5-tri-O-benzoyl-α-D-ribofuranose in the stereospecific synthesis of 2'-O-methylpyrimidine-β-D-ribonucleoside by the glycosilation of silylated bases, using Lewis acid as a catalyst. This procedure was optimized for large scale preparation of 2'-O-methylpyrimidine ribonucleosides by Ross et al., (*J. Hetercyclic Chem.* 31,765 1994). This procedure required methylation of 1,3,5-tri-O-benzoyl-α-D-ribofuranose with a large excess of potentially explosive diazomethane.

As an alternate, Applicant describes transglycosilation of suitably protected 2'-O-Me-pyrimidine ribonucleosides obtained through B(OMe)$_3$ mediated opening of 2,2'-anhydronycleosides. Transglycosylation reaction proceeds usually with high β-selectivity, if the carbohydrate donor contains a 2'-O-acyl group capable of stabilising the postulated C-1 carboxonium ion for exclusive β-attack by the incoming silylated base. The stereochemical outcome of transglycosilation reaction with carbohydrate donor, without the participating group at 2'-position (as 2'-O-Methyl) usually results in a mixture of α, and β nucleosides, as documented for the synthesis of 2'-N$_3$ purine ribonucleoside (Imazawa and Eckstein, 1979, *J. Org. Chem.* 44, 2039–41).

Applicant has investigated transglycosilation of 5',3'-di-O-acetyl-2'-O-Methyl uridine, obtained by the acylation of 2'-O-Methyl uridine. The transglycosilation of 5',3'-di-O-acetyl-2'-O-Methyl uridine with 3 eq of N$^6$-benzoylaminopurine and 3 eq TMStriflate in CH$_3$CN at 75° C. for 16 hour resulted in unseparable mixture of α and β isomers of N$^6$-Benzoyl-5',3'-di-O-acetyl-2'-O-methyl adenosine in ~60% yield and 1:1 ratio. Since the nature of aglycone can also influence product distribution in transglycosilation reaction (Azuma and Isono, 1977, *Chem. Pharm. Bull.* 25, 3347–53), we decided to try $N^4$-acetyl-5', 3'-di-O-acetyl-2'-O-methyl cytidine (2) as a carbohydrate donor. Suprisingly, utilization of this donor under the same conditions as described above for 2'-O-Methyl uridine derivative resulted in the exclusive formation of β anomer of $N^6$-Benzoyl-5',3'-di-O-acetyl-2'-O-methyl adenosine (3) in 50% yield. When $N^6$-phenoxyacetylaminopurine was used instead of $N^6$-Benzoyladenine under the same conditions described above, extensive decomposition of initially formed adenosine derivative was observed and target nucleoside was not isolated.

EXAMPLE 7

Synthesis of 2'-O-Methyl-Guanosine and Adenosine from 2-amino-6-chloropurine riboside (Scheme 2; FIG. 8)

High regioselectivity in methylation of 6-Cl-guanosine by diazomethane was reported by Robins' laboratory in 1966 (Khawaia and Robins, *J. Am. Chem. Soc.* 1966, 88, 3640–43). Despite the exclusive methylation of 2'-OH, the 2'-O-Methyl-6-Cl-guanosine was not isolated. Subsequent transformation of this key intermediate resulted in the preparation of 2'-O-methyl-guanosine in 30% yield. Moreover, the use of diazomethane as a methylation agent is not practical for large scale preparations. It was therefore reasonable to investigate other methylation reagents.

Suprisingly, Applicant has found that the methylation of 2-amino-6-chloropurine riboside with a small excess of NaH/MeI reagent in $CH_2Cl_2$ at −20° C. resulted in 2'-O-Me-6-Cl-guanosine in 65% yield along with the formation of 2',3' bis-O-Me derivative in 15% yield; no 3'-methylation was observed under these conditions. Several procedures were tested for the transformation of intermediate (5) into 2'-O-Methyl-guanosine (9). Applicant found that, the best result was obtained when intermediate (5) was treated with 1,4-diazabicyclo[2.2.2]octane (1 equiv.) and water (30 mL) at 90° C. for 45 minutes, followed by hydrolysis with 2M NaOH at pH 12 (FIG. 8). The desired 2'-O-Methyl-guanosine was obtained in 65% yield.

The surprisingly high regio-selectivity observed in the methylation of 2-amino-6-chloropurine riboside facilitates large scale synthesis of 2'-O-Me-6-Cl-guanosine, which can serve as a key intermediate in the preparation of not only 2'-O-Methyl-guanosine, but also 2'-O-Methyl-adenosine. This latter transformation was achieved through radical deamination (Nair and Richardson, *Synthesis,* 1982 670–672) of 3',5'-di-O-Acetyl-2'-O-Methyl-6-Chloro-2-aminopurine riboside (6) which yields 3',5'-di-O-Acetyl-2'-O-Methyl-6-Chloropurine (7) in 72% yield starting from 5. Subsequent amination of (7) with methanolic ammonia at 125° C. for 4 hours yields 2'-O-Methyl-adenosine (8) in 80% yield.

EXAMPLE 8

Synthesis of $N^2$-acyl(Isobutyryl and isopropylphenoxyacetyl)-2'-O-methylguanosine from 2,6-Diamino-β-D-ribofuranosylpurine (Scheme 3; FIG. 9)

It has been reported that the diazomethane methylation of 2,6-Diamino-β-D-ribofuranosylpurine in the presence of $SnCl_2 \times 2H_2O$ provided a 1:1 mixture of 2'- and 3'-O-methylated derivatives in a quantitative yield. These compounds can be separated on Dowex 1 $OH^-$ column and deaminated to the corresponding Guanosine derivatives with Adenosine Deaminase (Robins et al., *Can. J. Chem.* 1981, 59, 3360). It is also known in the literature that direct methylation of guanosine usually resulted in preferential methylation of $N_1$ and/or $N_7$ positions of the base. In 2,6-Diamino-β-D-ribofuranosylpurine, the acidic amide function C6-N1- is replaced by an basic amidine function, therefore one would expect that such a replacement should reduce the extent of methylation at N1 under basic conditions (i.e. NaH/MeI). In order to increase the regioselectivity, Applicant used 5',3'-O-tetraisopropyldisiloxane-1,3-diyl protection which has been reported to be relatively stable under NaH/MeI methylation conditions (Parmentier et al., 1994, *Tetrahedron,* 50, 5361–68).

The 5',3'-O-tetraisopropyldisiloxane-1,3-diyl protection was introduced by standard procedure, utilization of ethylacetate-water extraction allowed isolation of pure protected derivative (11) in 90% yield in crystalline form due to low solubility in above system.

Applicant has investigated several methylation procedures for the NaH/MeI system, including, varying the amount and the type of solvent and equivalents of NaH and MeI. Best results were obtained when methylation was performed at 0° C. in DMF with 1.5 eq of NaH and 3 eq. of MeI. If the reaction is performed at higher temperatures or in a more concentrated solution, extensive hypermethylation occured. Utilization of lower amounts of MeI required longer reaction time and resulted in the opening of cyclic silyl group with the simultaneous methylation of both 2' and 3' hydroxyl groups. The 2'-O-Methyl derivative 12 can then be isolated in 90% yield by crystallization and without any column chromatography (FIG. 9).

In order to synthesize $N^2$-acyl-2'-O-methylguanosine derivatives 14 and 15, Applicant tested selective acylation of $N^2$ amino group of intermediate 12 with subsequent chemical deamination of $N^6$ amino group. Two factors are critical for the success of this approach: the degree of selectivity in acylation of $N^2$ amino group vs $N^6$ amino group in intermediate 12 and the stability of $N^2$ protection under acidic conditions of deamination (Davoll et al., *J Am. Chem. Soc.* 1951, 73, 1650). Applicant has found that when the acylation of diamonopurine 12 is performed at −10° C. with 1.1 eq of acyl chloride, exclusive acylation of $N^2$ amino group in 12 occured (FIG. 9). For example, the $N^2$-isobutyryl intermediate 13 was isolated in 97% yield. The structure of 13 was confirmed by NMR data and by deamination to $N^2$-isobutyryl-2'-O-methylguanosine 14 with $NaNO_2$/$CH_3COOH$ followed by desilylation with TEA.3HF. Applicant also observed that during deamination with $NaNO_2$/$CH_3COOH$, 3',5'-O-cyclic silyl group opened, presumably at the 5'-position. This intermediate was not isolated but desilylated directly with TEA.3HF. It is worth noting that $N^2$-isobutyryl group was completely stable during deamination. The presence of hydrophobic silyl group in the intermediate allowed easy separation by extraction from excess of inorganic salts which made possible the subsequent desilylation without isolation.

High yields obtained in all the steps of transformation from 12 to 14 prompted us to combine these reactions in a "one pot" procedure without the isolation of intermediate 13. Selective acylation of 12 with isobutyryl chloride followed by deamination with $NaNO_2$/$CH_3COOH$ and desylilation with TEA.3HF resulted in $N^2$-isobutyryl-2'-O-methylguanosine 14 in 88% yield.

We also applied this procedure for the synthesis of $N^2$-isopropylphenoxyacetyl-2'-O-methylguanosine on a 50 g scale. The $N^2$-isopropylphenoxyacetyl protection was also stable under acidic deazotation conditions, although a minor loss of this group was observed resulting in a 83% overall yield starting from 12.

EXAMPLE 9

Synthesis of 2'-O-methylguanosine and 2'-O-Methyl-adenosine via metal-directed methylation
(Scheme 4; FIG. 10 and Table II)

It has been demonstrated that metal acetylacetonates can direct methylation of ribonucleosides with trimethylsulfonium hydroxide, mostly at the 2' and 3' hydroxyl groups of Uridine, Cytidine and Adenosine (Yamauchi et al., *J. Org Chem.* 1980, 45, 3865–68). Application of this procedure to the synthesis of Guanosine derivatives resulted in the isolation of 6 compounds with methylation in the base and the ribose moeties. When $N^1$-methyl-guanosine was subjected to the same methylation conditions 1,2' and 1,3' di-N-O methyl guanosines were isolated in 82% yield.

Applicant investigated procedures for metal-directed methylation of $N^1$-protected Guanosine with trimethylsulfonium hydroxide to optimize the ratio of 2':3' methylated products with subsequent separation and deblocking to obtain 2'-O-Methyl guanosine.

The protection of $N^1$ in guanosine was achieved using $N^1$ benzylation with N,N-dimethylformamide dibenzyl acetal (Philips and Horwitz *J. Org. Chem.* 1975, 40,1856). Applicant observed that complete cleavage of 2',3'-orthoamide required more drastic conditions than previously reported (2N NaOH vs MeOH/$NH_3$) (FIG. 10). The target compound was isolated in 80% yield after crystallization.

Several metal acetylacetonates were tested in methylation reaction (See Table I). Whereas $Cu^{2+}$ acetylacetonate mediated methylation produced 1:1 ratio of 2'- and 3'-O-methylated products; $Mg^{2+}$ and $Ag^+$ directed methylation changed the ratio to 9:1. With $Ag^+$ the overall conversion was higher than with $Mg^{2+}$ resulting in a 70% isolated yield of 2'-O-Me-$N_1$-Bzl-guanosine (FIG. 10; 17). The separation of 2'-O- and 3'-O-Me-$N_1$-Bzl-guanosine derivative was achieved on a preparative scale on Waters Delta-Pak ODS 50 mm×300 mm HPLC column. Removal of $N_1$-Bzl protection with $Na^+$ naphtalene provided 2'-O-Me-Guanosine in 90% yield.

Applicant investigated 12 different acetylacetonates in the direct methylation of Adenosine (Table II). Whereas Fe and Cu acetylacetonates provided 1:1 and 2:1 ration of 2' and 3' isomers as reported, Applicant discovered that $Ag^+$ and $Sr^{2+}$ allows equilibrium to shift towards 2'-isomer, providing 4:1 and 8:1 ratio. This allows the isolation of 2'-O-Me adenosine in 75–80% yield.

Experimental Procedures for the Synthesis of 2'-O-methyl Adenosine and Guanosine Nucleosides NMR spectra were recorded on a Varian Gemini 400 spectrometer operating at 400.075 MHz for proton and 161.947 MHz for phosphorus. Chemical shifts in ppm refer to TMS and $H_3PO_4$, respectively. Analytical thin-layer chromatography (TLC) was performed with Whatman MK6F silica gel 60 Å $F_{254}$ plates and column chromatography using Merck 0.040–0.063 mm Silica gel 60.
$N^6$-Benzoyl-5',3'-di-O-Acetyl-2'-O-Methyl adenosine (3):

To a solution of $N^4$-acetyl-2'-O-methyl cytidine(1) (1.87 g, 6.25 mmol) stirring at RT under argon in DMF/pyridine (20 ml, 20 ml) was added acetic anhydride (1.76 ml, 18.75 mmol) via syringe. The reaction mixture was stirred at RT for 18 hours then quenched with EtOH (2 ml). The reaction mixture was evaporated to dryness in vacuo and partitioned between dichloromethane and sat. $NaHCO_3$. The aqueous layer was back extracted with additional dichloromethane and the combined organics dried over $Na_2SO_4$. After filtration, the filtrate was evaporated in vacuo to afford a white foam.

A solution of $N^6$-benzoylaminopurine (Lancaster) (1.23 g, 5.16 mmol) stirring in anhydrous acetonitrile under an argon atmosphere was treated with BSA (3.82 ml, 15.48 mmol) at reflux for 3 hours. Upon cooling, a solution of $N^4$-acetyl-5',3'-di-O-acetyl-2'-O-methyl cytidine (2) (see above) (0.66 g, 1.72 mmol) in 20 ml anh. acetonitrile was added to the reaction mixture followed by TMStriflate (1.03 ml, 5.16 mmol). The reaction mixture was then heated to 75° C. for 16 hours while stirring under positive pressure argon. Upon cooling, an additional 1.03 ml (5.16 mmol) of TMStriflate was added, and the reaction heated to 75° C. for an additional 20 hours. Once cool, the reaction mixture was diluted with two volumes of dichloromethane and washed with sat. $NaHCO_3$. The organic layer was then dried over $Na_2SO_4$ and evaporated in vacuo. Flash chromatography employing a gradient of 10 to 80% ethyl acetate/hexanes afforded (1) as a white foam; 0.403 g, 50% yield. $^1$H NMR ($CDCl_3$): 8.88 (br s, 1H, NH), 8.81 (s, 1H, H8), 8.31 (s, 1H, H2), 8.11–7.53 (m, 5H, benzoyl), 6.18 (d, $J_{1',2'}=4.8$, 1H, H1'), 5.41 (t, $J_{3',2'}=4.8, J_{3',4'}=4.8$, 1H, H3'), 4.75 (t, $J_{2',1'}=4.8, J_{2',3'}=4.8$, 1H, H2'), 4.50–4.34 (m, 3H, H4', H5', H5"), 3.44 (s, 3H, $OCH_3$), 2.19 (s, 3H, OAc), 2.14 (s, 3H, OAc).

2'-O-Methyl-2-Amino-6-Chloropurine Riboside (5)

Sodium hydride. (0.44 g, 18.2 mmol) was added to the cooled (−20° C.) solution of 2-amino-6-chloropurine riboside 4 (5 g, 16.6 mmol) in dry dimethylformamide (100 mL) under stirring. After 1 hour the solution of $CH_3I$ (1.24 mL, 19.9 mmol) in dry dichloromethane (10 mL) was added dropwise to the reaction mixture during 1 hour. Resulted yellow solution was stirred at −20° C. for additional 2 hours until TLC (methylene chloride-methanol 9:1) showed complete disappearance of starting material. Reaction mixture was quenched with methanol (20 mL), warmed to the room temperature and evaporated to dryness in vacuo. The residue was dissolved in water (200 mL) and extracted with methylene chloride (3×200 mL). Organic layer was back extracted with water (100 mL). Combined aqueous phase was evaporated to dryness and the residue was purified by flash chromatography on silica using gradient of MeOH (7% to 10%) in methylene chloride to give 3.4 g (65%) of the compound 5. Flash chromatography purification can be substituted by multiple crystallization from acetonitrile, m.p. Calcd. for $C_{10}H_{12}N_5O_4Cl$ (301.69): C, 39.81; H, 4.01; N, 23.21; Cl, 11.75; found C; H; N; Cl. $^1$H-NMR (DMSO-$d_6$): 3.32 (3H, s, 2'-OMe); 3.578 (1H, dd, 5'-H, $J_{4',5'}$ 4.0, $J_{5',5'}$ 12.0); 3.66 (1H, dd, 5'-H, $J_{4',5'}$ 4.0, $J_{5',5'}$ 12.0); 3.949 (1H, dd, 4'-H, $J_{3',4'}$ 3.6); 4.252 (1H, t, 2'-H, $J_{2',3'}$ 4.0); 4.312 (1H, m, 3'-H); 5.073 (1H, bs, 3'-OH, exchangeable); 5.236 (1H, bs, 5'-OH, exchang-eable); 5.908 (1H, d, 1'-H, $J_{1',2'}$ 6.0); 6.964 (2H, bs, 2-$NH_2$); 8.391 (1H, s, 8-H).

2'-O-Methyl Guanosine (9)

A mixture of 5 (2.05 g, 6.5 mmol), 1,4-diazabicyclo [2.2.2]octane (1 equiv.) and water (30 mL) was heated to 90° C. for 45 minutes. Then the solution was cooled to ambient temperature, basified to pH 12 with 2M NaOH, and washed with methylene chloride (3×60 mL). The aqueous phase was acidified to pH 6 with 6M HCl and left at refrigerator overnight. Formed precipitate was filtered off. Mother liquor was evaporated to dryness, the residue was dissolved in water and applied to the short column with RP-18 silica gel.

Solid phase was washed with water and remaining product was eluted with 5% aq methanol. Appropriate fractions were combined, evaporated to dryness and recrystallized from to provide 1.25 g (65%) of 2'-O-methyl guanosine 9. Analytical sample was recrystalized from water, m.p. The product was identical to authentic sample by HPLC, UV, $^1$H-NMR-spectroscopy.

3',5'-di-O-Acetyl-2'-O-Methyl-6-Chloropurine Riboside (7)

To the solution of compound 5 (1.25 g, 3.96 mmol), 4-dimethylaminopyridine (39 mg, 0.32 mmol) and triethylamine (0.37 mL, 2.64 mmol) in dry acetonitrile was added acetic anhydride (0.9 mL, 9.5 mmol) and the reaction mixture was left at room temperature for 40 minutes. Then it was quenched with MeOH (10 mL) and evaporated to dryness. The residue was dissolved in methylene chloride and washed with 1% aq acetic acid, saturated aq sodium bicarbonate, and brine. The organic layer was dried over sodium sulfate and evaporated to dryness yielding acetate 6. The residue was additionally dried in vacuo for 3 hours, dissolved in dry THF and degassed with dry argon. To the above boiling solution under positive pressure of argon isoamylnitrite (10 eq) was added dropwise. After 2 hours solvent was removed in vacuo and the residue was dissolved in methylene chloride, washed with saturated aq NaHCO$_3$ and brine. The residue after evaporation of organic phase was purified by flash chromatography on silica gel. Elution with hexanes-ethyl acetate (1:1) mixture provided 1.1 g (72%) of compound 7 as yellow oil. Calcd. for $C_{15}H_{17}N_4O_6Cl$ (384.78): C, 46.82; H, 4.45; N, 14.56; Cl, 9.21; found C; H; N; Cl. $^1$H-NMR (CHCl$_3$-d): δ 2.133 (3H, s, 3'-OAc or 5'-OAc); 2.184 (3H, s, 3'-OAc or 5'-OAc); 3.44 (3H, s, 2'-OCH$_3$); 4.425 (3H, m, 4'-H, 5'-CH$_2$); 4.686 (1H, t, 2'-H, $J_{2',3'}$ 5.04); 5.36 (1H, t, 3'-H, $J_{3',4'}$ 4.28); 6.132 (1H, d, 1'-H, $J_{1',2'}$ 4.88); 8.311 (1H, s, 8-H); 8.771(1H, s, 2-H).

2'-O-Methyl Adenosine (8)

Solution of compound 7 (0.45 g, 1.17 mmol) in saturated methanolic ammonia (20 mL) was autoclaved at 125° C. for 4 hours. The solvent was removed in vacuo and remaining residue was purified by flash chromatography on silica gel. Elution with methylene chloride-methanol (9:1) mixture provided 0.25 g (80%) of 2'-O-methyl adenosine 8 as white solid. The analytical sample was recrystallized from abs EtOH. m.p. The product was identical to authentic sample by HPLC, UV-, $^1$H-NMR-spectroscopy.

2,6-Diamino-9-[3',5'-O-tetraisopropyldisiloxane-1,3-diyl)-β-D-ribofuranosyl]purine (11):

To an oven baked 500 ml three neck round bottom flask equipped with mechanical stirrer, positive pressure argon, and rubber septum was added 2,6-Diamino-9-(β-D-ribofuranosyl)purine (10) (10.0 g, 35.4 mmol), anhydrous DMF (100 ml), and anhydrous pyridine (200 ml). The resulting light brown suspension was cooled to 0° C. in an ice/water bath while stirring. TIPSCI (42.48 mmol, 13.6 ml) was added dropwise to the stirred 0° C. reaction mixture via syringe over a 20 minute period. The reaction mixture was then warmed to rt resulting in a homogeneous solution. TLC indicated complete reaction after 3 hours at rt, at which time the reaction was quenched by addition of ethanol (20 ml). The reaction mixture was then evaporated in vacuo and the resulting residue partitioned between ethyl acetate and sat. aqueous NaHCO$_3$ at which time (11) precipitated from the organic layer. The aqueous layer was then back extracted with ethyl acetate and the combined organics cooled to 0° C. The precipitate was filtered and washed with ethyl acetate to afford (11) as a beige solid; 16.5 g, 89% yield. $^1$H NMR (dmso-d6): 7.77 (s, 1H, H8), 6.75 (s, exch, 2H, N$^6$—NH$_2$), 5.74 (s, exch, 2H, N$^2$—NH$_2$), 5.71 (s, 1H, H1'), 5.56 (d, $J_{OH,2'}$=5.0, 1H, 2'-OH), 4.43 (dd, $J_{3',2'}$=4.5, $J_{3',4'}$=7.8, 1H, H3'), 4.29 (m, $J_{2',OH}$=5.0), 4.06–3.88 (m, 3H, H4', H5', H5"), 1.04 (m, 28H, TIPDS).

2,6-Diamino-9-[3',5'-O-tetraisopropyldisiloxane-1,3-diyl)-2'-O-methyl-β-D-ribofuranosyl]purine (12):

To an oven baked 500 ml three neck round bottom flask equipped with mechanical stirrer and positive pressure argon was added (11) (15.6 g, 29.7 mmol) followed by anhydrous DMF (300 ml) and methyl iodide (89.2 mmol, 5.55 ml). The reaction mixture was cooled to 0° C. in an ice/water bath and 60% sodium hydride in oil (44.6 mmol, 1.78 g) added slowly. A temperature of 0° C. was maintained for 35 minutes at which time the reaction was quenched with anhydrous ethanol and diluted into 2 volumes of 0°0 C. dichloromethane. The dilute reaction mixture was washed two times with sat. NH$_4$Cl, the aqueous layer back extracted with dicloromethane, and the combined organics dried over Na$_2$SO$_4$, filtered and evaporated to dryness in vacuo. Crystallization from ethanol/water 1:1 afforded 14.7 grams of (12), 92% yield.

$^1$H NMR (dmso-d6): 7.75 (s, 1H, H8), 6.76 (s, exch, 2H, N$^6$—NH$_2$), 5.78 (s, 1H, H1'), 5.73 (s, exch, 2H, N$^2$—NH$_2$), 4.58 (dd, $J_{3',2'}$=4.8, $J_{3',4'}$=4.8, 1H, H3'), 4.12 (d, $J_{2',3'}$=4.8), 4.09–3.91 (m, 3H, H4', H5', H5"), 3.54 (s, 3H, OCH$_3$), 1.03 (m, 28H, TIPDS).

2,6-Diamino-N$^2$-isobutyryl-9-[3',5'-O-tetraisopropyldisiloxane-1,3-diyl)-2'-O-methyl-β-D-ribofuranosyl]purine (13):

A solution of (3) (0.5 g, 0.93 mmol) in anhydrous pyridine (20 ml) was cooled to −10° C. in an ice/ethanol bath while stirring under argon. Isobutyryl chloride (1.02 mmol, 0.11 ml) was added dropwise to the stirred −10° C. solution over a period of 5 minutes. The reaction mixture was stirred at −10° C. for 2 hours followed by 1 hour at rt then quenched with ethanol (2 ml). After evaporating the reaction mixture to dryness in vacuo, the resulting residue was partitioned between dichloromethane and sat. aqueous NaHCO$_3$. The aqueous layer was back extracted with dichloromethane and the combined organics dried over Na$_2$SO$_4$. Filtration and evaporation of the filtrate in vacuo afforded a beige foam. Flash chromatography using a gradient of 2–4% ethanol in dichloromethane afforded (13) as a white foam; 0.55 g, 97% yield.

$^1$H NMR (dmso-d6): 9.76 (s, exch, 1H, N$^2$—NH), 8.04 (s, 1H, H8), 7.20 (s, exch, 2H, N$^6$—NH$_2$), 5.88 (s, 1H, H1'), 4.71 (dd, $J_{3',2'}$=5.2, $J_{3',4'}$=5.2, 1H, H3'), 4.26 (d, $J_{2',3'}$=5.2), 4.15–3.91 (m, 3H, H4', H5', H5"), 3.55 (s, 3H, OCH$_3$), 2.87 (m, 1H, iBu-CH), 1.06–0.96 (m, 34H, TIPDS, iBu-(CH$_3$)$_2$).

N$^2$-isobutylryl-2'-O-methylguanosine (14):

A solution of (13) (5.0 g, 9.28 mmol) in anhydrous pyridine (100 ml) was cooled to −10° C. in an ice/ethanol bath while stirring under argon. Isobutyryl chloride (10.21 mmol, 1.07 ml) was added dropwise to the stirred −10° C. solution over a period of 30 minutes. The reaction mixture was stirred at −10° C. for 2 hours followed by 1 hour at rt then quenched with ethanol (20 ml). After evaporating the reaction mixture to dryness in vacuo, the resulting residue was partitioned between dichloromethane and sat. NaHCO$_3$. The aqueous layer was back extracted with dichloromethane and the combined organics dried over Na$_2$SO$_4$. Filtration and evaporation of the filtrate in vacuo afforded a beige foam which was dissolved in glacial acetic acid (80 ml). To the stirred acetic acid solution was added water (40 ml) followed by NaNO$_2$ (74.24 mmol, 5.12 g). Another portion of NaNO$_2$ (74.24 mmol, 5.12 g) was added after 30 minutes and the reaction stirred at rt for 48 hours. The reaction mixture was diluted with one volume of n-butanol and evaporated in vacuo to 50% of the original volume. Co-evaporation with n-butanol (3x) was followed by partitioning the crude syrup between ethyl acetate and sat. aqueous $NaHCO_3$. After back extracting the aq. layer with ethyl acetate, the combined organics were evaporated to dryness in vacuo. The crude residue was then dissolved in anhydrous dichloromethane (50 ml) and treated with a solution of TEA.3HF (27.84 mmol, 4.54 ml) and TEA (8.17 ml), in dichloromethane (20 ml). The reaction mixture was evaporated to dryness in vacuo and subsequently dissolved in additional dichloromethane (20 ml). Evaporation followed by dilution was repeated 3 times, and the crude product purified by flash chromatography. A gradient of 2–10% ethanol in dichloromethane afforded (14) as light yellow foam; 3.02 g, 88% yield. $^1$H NMR (dmso-d6): 12.08 (s, exch, 1H, NH), 11.63 (s, exch, 1H, NH), 8.29 (s, 1H, H8), 5.90 (d, $J_{1',2'}$=6.3, 1H, H1'), 5.23 (d, $J_{OH,3'}$=4.9, 1H, 3'-OH), 5.07 (t, $J_{OH,5'}$=5.3, $J_{OH,5''}$=5.3, 1H, 5'-OH), 4.30 (m, $J_{3',2'}$=4.8, $J_{3',4'}$=3.3, 1H, H3'), 4.22 (t, $J_{2',1'}$=6.3, $J_{2',3'}$=4.8, 1H, H2'), 3.93 (m, $J_{4',3'}$=3.3, $J_{4',5'}$=3.9, $J_{4',5''}$=3.9, 1H, H4') 3.65–3.53 (m, 2H, H5', H5''), 3.33 (s, 3H, $OCH_3$), 2.78 (m, 1H, iBu-CH), 1.12 (d, 6H, iBu-$(CH_3)_2$).

$N^2$-isopropylphenoxyacetyl-2'-O-methylguanosine (15):

A solution of (12) (47.4 g, 88 mmol) in anhydrous pyridine (500 ml) was cooled to −10° C. in an ice/ethanol bath while stirring under argon. Isopropylphenoxyacetyl chloride (96.8 mmol, 20.6 ml) was added dropwise to the stirred −10° C. solution over a period of 5 minutes. The reaction mixture was stirred at −10° C. for 2 hours followed by 1 hour at rt then quenched with ethanol (20 ml). After evaporating the reaction mixture to dryness in vacuo, the resulting residue was partitioned between dichloromethane and sat. aqueous $NaHCO_3$. The aqueous layer was back extracted with dichloromethane and the combined organics dried over $Na_2SO_4$. Filtration and evaporation of the filtrate in vacuo afforded a beige foam which was dissolved in glacial acetic acid (1000 ml). To the stirred acetic acid solution was added water (400 ml) followed by $NaNO_2$ (742.4 mmol, 51.2 g). Another portion of $NaNO_2$ (742.4 mmol, 51.2 g) was added after 30 minutes and the reaction stirred at rt for 48 hours. The reaction mixture was diluted with one volume of n-butanol and evaporated in vacuo to 50% of the original volume. Co-evaporation with n-butanol (3x) was followed by partitioning the crude syrup between ethyl acetate and sat. aqueous $NaHCO_3$. After back extracting the aq. layer with ethyl acetate, the combined organics were evaporated to dryness in vacuo. The crude residue was then dissolved in anhydrous dichloromethane (500 ml) and treated with a solution of TEA.3HF (278.4 mmol, 45.4 ml) and TEA (81.7 ml), in dichloromethane (200 ml). The reaction mixture was evaporated to dryness in vacuo and subsequently dissolved in additional dichloromethane (200 ml). Evaporation followed by dilution was repeated 3 times, and the crude product purified by flash chromatography. A gradient of 2–10% ethanol in dichloromethane afforded (5) as light yellow foam; 29.2 g, 85% yield. $^1$H NMR (dmso-d6): 11.65 (s, exch, 2H, NH, NH), 8.30 (s, 1H, H8), 7.18–6.88 (dd, 4H, phenoxy), 5.91 (d, $J_{1',2'}$=6.0, 1H, H1'), 5.24 (d, $J_{OH,3'}$=4.8, 1H, 3'-OH), 5.09 (t, $J_{OH,5'}$=5.6, $J_{OH,5''}$=5.2, 1H, 5'-OH), 4.82 (s, 2H, $CH_2$), 4.31 (m, $J_{3',2'}$=4.8, $J_{3',4'}$=3.6, 1H, H3'), 4.23 (t, $J_{2',1'}$=6.0, $J_{2',3'}$=4.8, 1H, H2'), 3.93 (m, $J_{4',3'}$=3.6, $J_{4',5'}$=4.0, $J_{4',5''}$=3.9, 1H, H4') 3.65–3.53 (m, 2H, H5', H5''), 3.35 (s, 3H, $OCH_3$), 2.84 (m, 1H, iPr-CH), 1.17 (d, 6H, iPr-$(CH_3)_2$).

N1-Benzyl guanosine (16)

Guanosine hydrate (50 grams, 177 mmol) was coevaporated twice from dimethylformamide (2×250 ml) and dissolved in dry dmf (400 mls). N,N-dimethylformamide dibenzyl acetal was added (240 grams, 230 ml, 885 mmol) and the solution was heated with stirring to 80° C. for 18 hrs. The excess acetal was removed by steam distillation on a rotary evaporator. The product was recovered without chromatography by washing with dichloromethane/hexanes (1:1 v/v) to yield 84 g of the ortho-amide intermediate. The o ortho-amide was cleaved by treatment with aqueous sodium hydroxide (2N, 133 ml) at room temperature for four hours. The product was recrystallized from boiling water to yield 54 g (145 mmol, 82%) of pure (16). $^1$H NMR (dmso-d$_6$): 7.97 (s, 1H, H8), 7.29 (m, 5H, Bz), 7.02 (bs, 2H, $2NH_2$), 5.70 (d, $J_{1',2'}$=5.6, 1H, H1'), 5.42 (bs, 1H, 2'OH), 5.23 (s, 1H, $CH_2$-Bz), 5.15 (bs, 1H, 3'OH), 5.00 (bs, 1H, 5'-OH), 4.41 (t, $J_{3',2'}$=5.6, $J_{3',4'}$=4.0, 1H, H3'), 4.08 (t, $J_{2',1'}$=6.3, $J_{2',3'}$=4.8, 1H, H2'), 3.85 (m, $J_{4',3'}$=3.5, $J_{4',5'}$=4.0, 1H, H4') 3.58–3.49 (m, 2H, H5', H5'').

N1-Benzyl-2'-O-Methyl Guanosine (17)

A 1 L pear shaped recovery flask with stir bar was charged with a mixture of 16 (50 g, 134 mmol), silver acetylacetonate (41 g 200 mmol), TMSH (200 ml of 1N solution in methanol) and dimethylformamide (400 ml). The flask was heated to 70° C. for two hours. The solution was cooled to ambient temperature, neutralized to pH 7 with 1M HCl, and dried to a solid tar. The tar was dissolved in water (500 ml) and filtered through a sintered glass funnel to remove silver salts. The product was evaporated to dryness to remove water and residual solvents and 10 grams (26 mmols) was redissolved in 50 ml of water prior to purification on a Waters Delta-Pak ODS 50 mm×300 mm HPLC column. The N1-Bz-2'-OMe guanosine isomer eluted first and was recovered using a rotary evaporator. The product (7 g, 18 mm, 70%) was identical to an authentic sample by HPLC, UV-, $^1$H-NMR-spectroscopy. $^1$H NMR (dmso-d$_6$): 8.02 (s, 1H, H8), 7.26 (m, 5H, ph), 7.02 (bs, 2H, 2NH2), 5.82 (d, $J_{1',2'}$=6.4, 1H, H1'), 5.23 (s, 2H, CH2-Bz), 5.18 (d, $J_{OH,3'}$=4.8, 1H, 3'-OH), 5.04 (t, $J_{OH,5'}$=5.2, $J_{OH,5''}$=5.6, 1H, 5'-OH), 4.28 (m, $J_{3',2'}$=4.8, $J_{3',4'}$=3.2, 1H, H3'), 4.20 (t, $J_{2',1'}$=6.4, $J_{2',3'}$=4.8, 1H, H2'), 3.90 (m, $J_{4',3'}$=3.6, $J_{4',5'}$=4.0, 1H, H4'), 3.65–3.53 (m, 2H, H5', H5'' $J_{OH,5'}$=5.2, $J_{5',5''}$=11.6), 3.33 (s, 3H, $OCH_3$).

2'-O-Methyl Guanosine (9)

Sodium spheres (3.5 grams) in mineral oil were washed with hexanes and weighed into dry THF. A glass bottle with polyethylene closure was charged with naphthalene (21.2 g, scintillation grade), dry THF (210 ml) and a glass sealed stir bar. The sodium was added and the mixture was stirred vigorously for one hour. The solution turned dark green after ten minutes and all sodium was presumed to be consumed after one hour to yield 150 mm of 0.6M sodium naphthalene solution. This solution was used without further characterization. A 250 ml flask was charged with $N_1$Bzl-2'-O-methyl guanosine (2 g, 5.0 mm) and a glass sealed stir bar. Sodium naphthalene solution was added (50 mmol, 90 ml) and the solution was stirred overnight. TLC (10% MeOH in DCM) showed complete deblock of the benzyl group. The reaction was quenched with 10 mls of methanol and all solvents were removed with a rotary evaporator. Water (100 ml) was added and the solution was neutralized with HCl (1N, pH 7, 50 ml). Naphthalene was removed with extraction by toluene (3×100 mls) and the solution was pumped over an ODS Delta-Pak column to recover 2'-O-Me guanosine nucleoside. The product (1.3 g, 4.5 mmol, 90%) was identical to an authentic sample by HPLC, UV-Vis & $^1$H-NMR-spectroscopy.

Trimethylsulfonium Hydroxide (TMSH) Solution in Methanol:

A 0.2 M solution of trimethyl sulfonium iodide (TMSI, 102 grams, 0.5 mol), in 2.5 L of methanol and water (9:1, v/v) was prepared by heating to 40 C and mixing continuously for 30 min. The clear, colorless solution was allowed to cool to r.t. A glass chromatography column (Ace #50 thread; 75 mm×300 mm) containing Duolite 147 anion exchange resin (900 g) in the hydroxide form was previously packed and used for the conversion of TMSI to TMSH. The solution was pumped over the column using a gear pump at 100 ml per minute. The resin was washed with an additional 1 liter of 90% methanol and the total 3.5 liters was reduced in volume to 500 ml using a rotary evaporator with the bath set at 20° C. The solution was checked for the presence of iodide ion using acidified silver nitrate solution and found to be negative. The solution was not characterized further and was stored in a teflon bottle with a gas vent at 5° C.

2'-O-Methyl Adenosine (8)

A solution of adenosine (50 g, 187 mmol) in dimethylformamide (400 ml) was prepared by heating to 50° C. with continuous mixing for 10 minutes in a 1 L pear shaped recovery flask containing a stir bar. Silver acetylacetonate (58 g, 280 mmol) and TMSH (280 ml of a 1 M) solution was added and the mixture was stirred immediately. The reaction mixture was heated to 75° C. With stirring for 45 minutes. A sample of the mixture showed no starting adenosine and two spots of which the predominant one comigrates with an authentic sample of 2'-OMe adenosine. An HPLC assay showed an nine to one ratio for 2' to 3'-OMe adenosine The solvent was removed by rotary evaporation and 500 ml of water and 250 ml of 1N HCl was added to neutralize the hydroxide (pH 7 by Hydrion strips) prior to filtration on a sintered glass funnel. The water and solvents were removed by rotary evaporation leaving a brown tar. This material was purified on a ODS 25 mm×300 mm Delta-Pak HPLC column using water as the eluant. Overall recovery of 42 grams for a yield of 75% from adenosine. The product 12 was identical to authentic sample by HPLC, UV-, $^1$H-NMR-spectroscopy.

These examples are meant to be non-limiting and those skilled in the art will recognize that similar strategies, as described in the present invention, can be readily adapted to synthesize other methoxy nucleosides and nucleoside analogs and are within the scope of this invention.

Other embodiments are within the following claims.

TABLE I

Methylation of $N^1$-Benzyl Guanosine with acethylacetonates

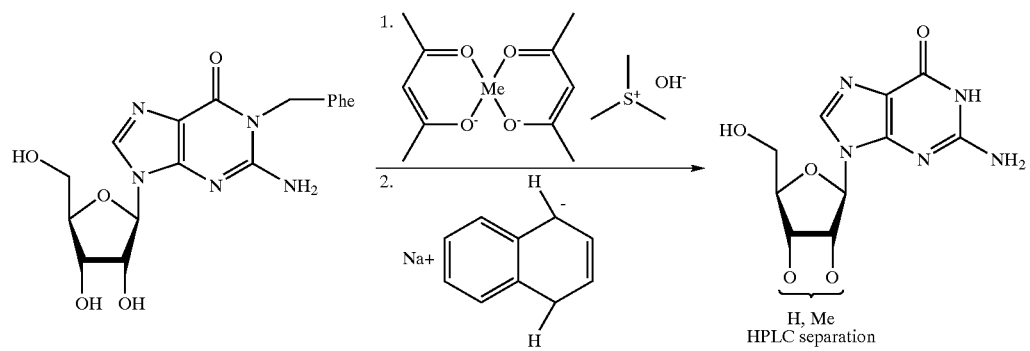

| Metal | 2'-O—Me-G$^{bzl}$ | 3'O—Me-G$^{bzl}$ | 2'-O—Me-G yield |
|---|---|---|---|
| Cu | 40 | 42 | 32 |
| Mg | 65 | 7 | 45 |
| Ag | 70 | 8 | 70 |

TABLE II

Metal-Directed methylation of Adenosine

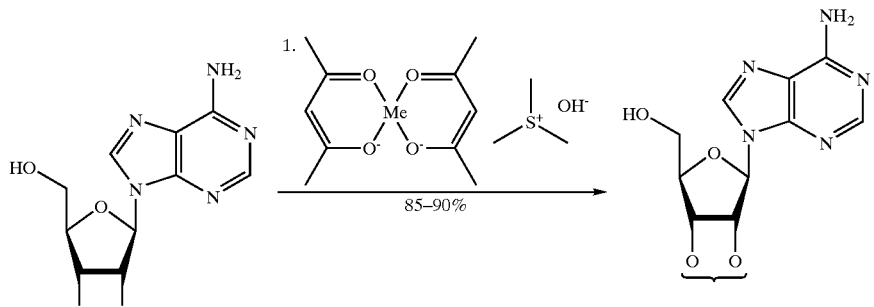

| Metal | 2'-O—Me-A | 3'-O—Me-A | 2'-O—Me-A yield |
|-------|-----------|-----------|-----------------|
| Fe    | 1         | 1         | 45%             |
| Cu    | 2         | 1         | 60%             |
| Ag    | 4         | 1         | 72%             |
| Sr    | 8         | 1         | 80%             |

What is claimed is:

1. A process for the synthesis of a 2'-O-methyl adenosine nucleoside phosphoramidite, comprising the steps of
   a) contacting a solution of N4-acetyl-5',3'-di-O-acetyl-2'-O-methyl cytidine with a Lewis acid under conditions suitable for formation of 2'-O-methyl adenosine nucleoside, and
   b) converting the 2'-O-methyl adenosine nucleoside to a 2'-O-methyl adenosine nucleoside phosphoramidite under conditions suitable for formation of said 2'-O-methyl adenosine nucleoside phosphoramidite.

2. A process for the synthesis of 2'-O-methyl guanosine nucleoside phosphoramidite, comprising the steps of:
   a) methylating 2-amino-6-chloropurine riboside by contacting said 2-amino-6-chloropurine riboside with sodium hydride, dimethylformamide and methyl iodide under conditions suitable for formation of 2'-O-methyl-2-amino-6-chloropurine riboside;
   b) contacting said 2'-O-methyl-2-amino-6-chloropurine riboside with 1,4-diazabicyclo(2.2.2) octane and water under conditions suitable for formation of said 2'-O-methyl guanosine nucleoside in a crude form;
   c) purifying 2'-O-methyl guanosine nucleoside from said crude form; and
   d) converting said 2'-O-methyl guanosine nucleoside to a 2'-O-methyl guanosine nucleoside phosphoramidite under conditions suitable for formation of said 2'-O-methyl guanosine nucleoside phosphoramidite.

3. A process for the synthesis of 2'-O-methyl adenosine nucleoside phosphoramidite, comprising the steps of:
   a) methylating 2-amino-6-chloropurine riboside by contacting said 2-amino-6-chloropurine riboside with sodium hydride, dimethylformamide and methyl iodide under conditions suitable for formation of 2'-O-methyl-2-amino-6-chloropurine riboside;
   b) contacting said 2'-O-methyl-2-amino-6-chloropurine riboside with acetic anhydride, 4-dimethylaminopyridine and triethylamine under conditions suitable for formation of 3',5'-di-O-acetyl-2'-O-methyl-6-chloro-2-aminopurine riboside;
   c) deaminating said 3',5'-di-O-acetyl-2'-O-methyl-6-chloro-2-aminopurine riboside with isoamyl nitrite and tetrahydrofuran to form 3',5'-di-O-acetyl-2'-O-methyl-6'-chloropurine;
   d) aminating said 3',5'-di-O-acetyl-2'-O-methyl-6-chloropurine with ammonia to form 2'-O-methyl adenosine nucleoside in a crude form;
   e) purifying said 2'-O-methyl adenosine nucleoside from said crude form; and
   f) converting said 2'-O-methyl adenosine nucleoside to a 2'-O-methyl adenosine nucleoside phosphoramidite under conditions suitable for formation of said 2'-O-methyl adenosine nucleoside phosphoramidite.

4. A process for the synthesis of N2-isobutyryl-2'-O-methyl guanosine nucleoside phosphoramidite, comprising the steps of:
   a) contacting 2,6-diaminopurine nucleoside with anhydrous pyridine and 1,3-dichloro-1,1,3,3-tetraisopropyldisiloxane under conditions suitable for formation of 2,6-diamino-9-(3,5-O-tetraisopropyidisiloxan-(1,3-diyl)-beta-D-ribofuranosyl) purine;
   b) methylating said 2,6-diamino-9-(3,5-O-tetraisopropyldisiloxan-(1,3-diyl)-beta-D-ribofuranosyl) purine by contacting said 2,6-diamino-9-(3,5-O-tetraisopropyldisiloxan-(1,3-diyl)-beta-D-ribofuranosyl) purine with anhydrous DMF and methyl iodide under conditions suitable for formation of 2,6-diamino-9-(3,5-O-tetraisopropyldisiloxan-(1,3-diyl)-2'-O-methyl-beta-D-ribofuranosyl) purine;
   c) acylating said 2,6-diamino-9-(3,5-O-tetraisopropyldisiloxan-(1,3-diyl)-2-O-methyl-beta-D-ribofuranosyl) purine by contacting said 2,6-diamino-9-(3,5-O-tetraisopropyldisiloxan-(1,3-diyl)-2-O-methyl-beta-D-ribofuranosyl) purine with anhydrous pyridine and isobutyryl chloride under conditions suitable for formation of 2,6-diamino-N2-isobutyryl-9-(3,5-O-tetraisopropyldisiloxan-(1,3-diyl)-2-O-methyl-beta-D-ribofuranosyl) purine;
   d) deaminating and desilylating said 2,6-Diamino-N2-isobutyryl-9-(3,5-O-tetraisopropyldisiloxan-(1,3-diyl)-2-O-methyl-beta-D-ribofuranosyl) purine under conditions suitable for formation of N2-isobutyryl-2'-O-methyl guanosine nucleoside in a crude form;

e) purifying said N2-isobutyryl-2'-O-methyl guanosine nucleoside from said crude form; and f) converting said N2-isobutyryl-2'-O-methyl guanosine nucleoside to a N2-isobutyryl-2'-O-methyl guanosine nucleoside phosphoramidite under conditions suitable for formation of said N2-isobutyryl-2'-O-methyl guanosine nucleoside phosphoramidite.

5. A process for the synthesis of N2-isopropylphenoxyacetyl-2'-O-methyl guanosine nucleoside phosphoramidite, comprising the steps of:

a) contacting 2,6-diaminopurine nucleoside with anhydrous pyridine and 1,3-dichloro-1,1,3,3-tetraisopropyldisiloxane (TIPSCI) under conditions suitable for formation of 2,6-diamino-9-(3',5'-O-tetraisopropyldisiloxan-(1,3-diyl)-beta-D-ribofuranosyl) purine;

b) methylating said 2,6-diamino-9-(3,5-O-tetraisopropyldisiloxan-(1,3-diyl)-beta-D-ribofuranosyl) purine by contacting said 2,6-diamino-9-(3,5-O-tetraisopropyldisiloxan-(1,3-diyl)-beta-D-ribofuranosyl) purine with anhydrous DMF and methyl iodide under conditions suitable for formation of 2,6-diamino-9-(3',5'-O-tetraisopropyldisiloxan-(1,3-diyl)-2'-O-methyl-beta-D-ribofuranosyl) purine;

c) acylating said 2,6-diamino-9-(3,5-O-tetraisopropyldisiloxan-(1,3-diyl)-2-O-methyl-beta-D-ribofuranosyl) purine by contacting said 2,6-diamino-9-(3,5-O-tetraisopropyldisiloxan-(1,3-diyl)-2-O-methyl-beta-D-ribofuranosyl) purine with anhydrous pyridine and isopropylphenoxyacetyl chloride under conditions suitable for formation of 2,6-diamino-N2-isopropylphenoxyacetyl-9-(3,5-O-tetraisopropyldisiloxan-(1,3-diyl)-2-O-methyl-beta-D-ribofuranosyl) purine;

d) deaminating and desilylating said 2,6-diamino-N2-isopropylphenoxyacetyl-9-(3,5-O-tetraisopropyldisiloxan-(1,3-diyl)-2-O-methyl-beta-D-ribofuranosyl) purine under conditions suitable for formation of N2-isopropylphenoxyacetyl-2'-O-methyl guanosine nucleoside in a crude form;

e) purifying said N2-isopropylphenoxyacetyl-2'-O-methyl guanosine nucleoside from said crude form; and f) converting said N2-isopropylphenoxyacetyl-2'-O-methyl guanosine nucleoside to a N2-isopropylphenoxyacetyl-2'-O-methyl guanosine nucleoside phosphoramidite under conditions suitable for formation of said N2-isopropylphenoxyacetyl-2'-O-methyl guanosine nucleoside phosphoramidite.

6. A process for the synthesis of 2'-O-methyl guanosine nucleoside phosphoramidite, comprising the steps of:

a) contacting guanosine with N,N-dimethylformamide dibenzyl acetal under conditions suitable for formation of N1-benzyl guanosine;

b) methylating said N1-benzyl guanosine by contacting said N1-benzyl guanosine with silver acetylacetonate, trimethylsulphonium hydroxide and dimethylformamide under conditions suitable for formation of N1-benzyl-2'-O-methyl guanosine in a crude form;

c) purifying said N1-benzyl-2'-O-methyl guanosine from said crude form;

d) removing the N1-benzyl protection from said N1-benzyl-2'-O-methyl guanosine by contacting said N1-benzyl-2'-O-methyl guanosine with sodium naphthalene under conditions suitable for formation of 2'-O-methyl guanosine nucleoside in a crude form;

e) purifying said 2'-O-methyl guanosine nucleoside from said crude form; and f) converting said 2'-O-methyl guanosine nucleoside to a 2'-O-methyl guanosine nucleoside phosphoramidite under conditions suitable for formation of said 2'-O-methyl guanosine nucleoside phosphoramidite.

7. A process for the synthesis of 2'-O-methyl adenosine nucleoside phosphoramidite, comprising the steps of:

a) methylating adenosine by contacting said adenosine with dimethylformamide, silver acetylacetonate and trimethylsulphonium hydroxide under conditions suitable for formation of 2'-O-methyl adenosine nucleoside in a crude form;

b) purifying said 2'-O-methyl adenosine nucleoside from said crude form; and c) converting said 2'-O-methyl adenosine nucleoside to a 2'-O-methyl adenosine nucleoside phosphoramidite under conditions suitable for formation of said 2'-O-methyl adenosine nucleoside phosphoramidite.

8. A process for the synthesis of 2'-O-methyl guanosine nucleoside phosphoramidite, comprising the steps of:

a) contacting guanosine with N,N-dimethylformamide dibenzyl acetal under conditions suitable for formation of N1-benzyl guanosine;

b) methylating said N1-benzyl guanosine by contacting said N1-benzyl guanosine with magnesium acetylacetonate, trimethylsulphonium hydroxide and dimethylformamide under conditions suitable for formation of N1-benzyl-2'-O-methyl guanosine in a crude form;

c) purifying said N1-benzyl-2'-O-methyl guanosine from said crude form;

d) removing the N1-benzyl protection from said N1-benzyl-2'-O-methyl guanosine by contacting said N1-benzyl-2'-O-methyl guanosine with sodium naphthalene under conditions suitable for formation of 2'-O-methyl guanosine nucleoside in a crude form;

e) purifying said 2'-O-methyl guanosine nucleoside from said crude form; and f) converting said 2'-O-methyl guanosine nucleoside to a 2'-O-methyl guanosine nucleoside phosphoramidite under conditions suitable for formation of said 2'-O-methyl guanosine nucleoside phosphoramidite.

9. A process for the synthesis of 2'-O-methyl adenosine nucleoside phosphoramidite, comprising the steps of:

a) methylating adenosine by contacting said adenosine with dimethylformamide, magnesium acetylacetonate and trimethylsulphonium hydroxide under conditions suitable for formation of 2'-O-methyl adenosine nucleoside in a crude form;

b) purifying said 2'-O-methyl adenosine nucleoside from said crude form; and c) converting said 2'-O-methyl adenosine nucleoside to a 2'-O-methyl adenosine nucleoside phosphoramidite under conditions suitable for formation of said 2'-O-methyl adenosine nucleoside phosphoramidite.

10. A process for the synthesis of 2'-O-methyl adenosine nucleoside phosphoramidite, comprising the steps of:

a) methylating adenosine by contacting said adenosine with dimethylformamide, strontium acetylacetonate and trimethylsulphonium hydroxide under conditions suitable for formation of 2'-O-methyl adenosine nucleoside in a crude form;

b) purifying said 2'-O-methyl adenosine nucleoside from said crude form; and c) converting said 2'-O-methyl adenosine nucleoside to a 2'-O-methyl adenosine nucleoside phosphoramidite under conditions suitable for formation of said 2'-O-methyl adenosine nucleoside phosphoramidite.

11. A process for the synthesis of N2-isobutyryl-2'-O-methyl guanosine nucleoside phosphoramidite, comprising the steps of:
   a) contacting 2,6-diaminopurine nucleoside with anhydrous pyridine and TIPSCI under conditions suitable for formation of 2,6-diamino-9-(3',5'-O-tetraisopropyldisiloxan-(1,3-diyl)-.beta.-D-ribofuranosyl) purine;
   b) methylating said 2,6-diamino-9-(3,5-O-tetraisopropyldisiloxan-(1,3-diyl)-beta-D-ribofuranosyl) purine by contacting said 2,6-diamino-9-(3',5'-O-tetraisopropyldisiloxan-(1,3-diyl)-beta-D-ribofuranosyl) purine with anhydrous DMF and methyl iodide under conditions suitable for formation of 2,6-diamino-9-(3,5-O-tetraisopropyldisiloxan-(1,3-diyl)-2-O-methyl-beta-D-ribofuranosyl) purine;
   c) acylating said 2,6-diamino-9-(3,5-O-tetraisopropyldisiloxan-(1,3-diyl)-2-O-methyl-beta-D-ribofuranosyl) purine by contacting said 2,6-diamino-9-(3,5-O-tetraisopropyldisiloxan-(1,3-diyl)-2-O-methyl-beta-D-ribofuranosyl) purine with anhydrous pyridine and isobutyryl chloride under conditions suitable for formation of 2,6-diamino-N2-isobutyryl-9-(3,5-O-tetraisopropyldisiloxan-(1,3-diyl)-2-O-methyl-beta-D-ribofuranosyl) purine;
   d) deaminating and desilylating said 2,6-diamino-N2-isobutyryl-9-(3,5-O-tetraisopropyldisiloxan-(1,3-diyl)-2'-O-methyl-beta-D-ribofuranosyl) purine under conditions suitable for formation of N2-isobutyryl-2'-O-methyl guanosine nucleoside in a crude form;
   e) purifying said N2-isobutyryl-2'-O-methyl guanosine nucleoside from said crude form; and
   f) converting said N2-isobutyryl-2'-O-methyl guanosine nucleoside to a N2-isobutyryl-2'-O-methyl guanosine nucleoside phosphoramidite under conditions suitable for formation of said N2-isobutyryl-2'-O-methyl guanosine nucleoside phosphoramidite.

12. A process for the synthesis of N2-isopropylphenoxyacetyl-2'-O-methyl guanosine nucleoside phosphoramidite, comprising the steps of:
   a) contacting 2,6-diaminopurine nucleoside with anhydrous pyridine and TIPSCI under conditions suitable for formation of 2,6-diamino-9-(3,5-O-tetraisopropyldisiloxan-(1,3-diyl)-beta-D-ribofuranosyl) purine;
   b) methylating said 2,6-diamino-9-(3,5-O-tetraisopropyldisiloxan-(1,3-diyl)-beta-D-ribofuranosyl) purine by contacting said 2,6-diamino-9-(3,5-O-tetraisopropyldisiloxan-(1,3-diyl)-beta-D-ribofuranosyl) purine with anhydrous DMF and methyl iodide under conditions suitable for formation of 2,6-diamino-9-(3,5-O-tetraisopropyldisiloxan-(1,3-diyl)-2-O-methyl-beta-D-ribofuranosyl) purine;
   c) acylating said 2,6-diamino-9-(3,5-O-tetraisopropyldisiloxan-(1,3-diyl)-2-O-methyl-beta-D-ribofuranosyl) purine by contacting said 2,6-diamino9-(3,5-O-tetraisopropyldisiloxan-(1,3-diyl)-2'-O-methyl-beta-D-ribofuranosyl) purine with anhydrous pyridine and isopropylphenoxyacetyl chloride under conditions suitable for formation of 2,6-Diamino-N2-isopropylphenoxyacetyl-9-(3',5'-O-tetraisopropyldisiloxan-(1,3-diyl)-2'-O-methyl-beta-D-ribofuranosyl) purine;
   d) deaminating and desilylating said 2,6-diamino-N2-isopropylphenoxyacetyl-9-(3,5-O-tetraisopropyldisiloxan-(1,3-diyl)-2-O-methyl-beta-D-ribofuranosyl) purine under conditions suitable for formation of N2-isopropylphenoxyacetyl-2'-O-methyl guanosine nucleoside in a crude form;
   e) purifying said N2-isopropylphenoxyacetyl-2'-O-methyl guanosine nucleoside from said crude form; and
   f) converting said N2-isopropylphenoxyacetyl-2'-O-methyl guanosine nucleoside to a N2-isopropylphenoxyacetyl-2'-O-methyl guanosine nucleoside phosphoramidite under conditions suitable for formation of said N2-isopropylphenoxyacetyl-2'-O-methyl guanosine nucleoside phosphoramidite.

* * * * *